US012642821B2

(12) United States Patent
Cani et al.

(10) Patent No.: US 12,642,821 B2
(45) Date of Patent: *Jun. 2, 2026

(54) **USE OF *AKKERMANSIA* FOR TREATING METABOLIC DISORDERS**

(71) Applicant: COMPAGNIE GERVAIS DANONE, Gif-sur-Yvette (FR)

(72) Inventors: Patrice Cani, Brussels (BE); Amandine Everard, Ottignies (BE); Clara Belzer, Wageningen (NL); Willem De Vos, Ede (NL)

(73) Assignee: COMPAGNIE GERVAIS DANONE, Gif-sur-Yvette (FR)

( * ) Notice: Subject to any disclaimer, the term of this patent is extended or adjusted under 35 U.S.C. 154(b) by 0 days.

This patent is subject to a terminal disclaimer.

(21) Appl. No.: 19/224,071

(22) Filed: May 30, 2025

(65) Prior Publication Data

US 2025/0288622 A1     Sep. 18, 2025

Related U.S. Application Data

(63) Continuation of application No. 14/443,829, filed as application No. PCT/EP2013/073972 on Nov. 15, 2013.

(30) Foreign Application Priority Data

Nov. 19, 2012     (WO) ................ PCT/EP2012/073011

(51) Int. Cl.
| | |
|---|---|
| *A61P 37/04* | (2006.01) |
| *A61K 9/00* | (2006.01) |
| *A61K 35/74* | (2015.01) |
| *A61K 35/741* | (2015.01) |

(52) U.S. Cl.
CPC ............ *A61K 35/74* (2013.01); *A61K 9/0053* (2013.01); *A61K 35/741* (2013.01); *Y02A 50/30* (2018.01)

(58) Field of Classification Search
CPC .... A61K 35/74; A61K 9/0053; A61K 35/741; A61K 2300/00; A61P 3/00; A61P 3/04; A61P 3/06; A61P 3/10; A61P 9/00; A61P 25/00; A61P 37/02; A61P 37/04; A61P 43/00; A61P 37/00
See application file for complete search history.

(56) References Cited

U.S. PATENT DOCUMENTS

| | | | |
|---|---|---|---|
| 7,253,333 | B2 | 8/2007 | Tanaka et al. |
| 9,173,910 | B2 | 11/2015 | Kaplan et al. |
| 9,895,341 | B2 | 2/2018 | Khoo et al. |
| 10,149,867 | B2 | 12/2018 | Kaplan et al. |
| 10,149,870 | B2 | 12/2018 | Kaplan et al. |
| 10,286,026 | B2 | 5/2019 | Israelsen et al. |
| 10,736,924 | B2 | 8/2020 | Cani et al. |
| 10,738,089 | B2 | 8/2020 | Belzer et al. |
| 11,466,057 | B2 | 10/2022 | Belzer et al. |
| 2005/0180962 | A1 | 8/2005 | Eyal et al. |
| 2005/0220907 | A1 | 10/2005 | Theoharides et al. |
| 2006/0094649 | A1 | 5/2006 | Keogh et al. |
| 2006/0147600 | A1 | 7/2006 | Gonzales et al. |
| 2009/0263466 | A1 | 10/2009 | Managoli et al. |
| 2010/0172874 | A1 | 7/2010 | Turnbaugh et al. |
| 2012/0083514 | A1 | 4/2012 | Prevost et al. |
| 2013/0224155 | A1 | 8/2013 | Kaplan et al. |
| 2015/0306152 | A1 | 10/2015 | Cani et al. |
| 2017/0028012 | A1 | 2/2017 | Faria et al. |
| 2018/0250347 | A1 | 9/2018 | Cani et al. |
| 2018/0265554 | A1 | 9/2018 | Belzer et al. |
| 2019/0046590 | A1 | 2/2019 | Kaplan et al. |
| 2019/0282630 | A1 | 9/2019 | Cani et al. |
| 2020/0121737 | A1 | 4/2020 | Cani et al. |
| 2020/0155616 | A1 | 5/2020 | Cani et al. |
| 2020/0237832 | A1 | 7/2020 | Cani et al. |
| 2020/0237833 | A1 | 7/2020 | Cani et al. |
| 2021/0015876 | A1 | 1/2021 | Cani et al. |
| 2021/0147489 | A1 | 5/2021 | Belzer et al. |
| 2021/0322489 | A1 | 10/2021 | Cani et al. |
| 2021/0393704 | A1 | 12/2021 | Cani et al. |

FOREIGN PATENT DOCUMENTS

| | | |
|---|---|---|
| CA | 3094903 A1 | 9/2019 |
| CA | 3110996 A1 | 3/2020 |
| CN | 110604833 A | 12/2019 |
| EP | 2030623 A1 | 3/2009 |
| JP | 2014-5017487 A5 | 2/2015 |
| WO | WO 2001/058283 A1 | 8/2001 |

(Continued)

OTHER PUBLICATIONS

Aggarwal et al., "Targeting Inflammatory Pathways for Prevention and Therapy of Cancer: Short-Term Friend, Long-Term Foe", Molecular Pathways, Clin Cancer Research, Jan. 15, 2009, 15(2): 425-430.
Alhouayek et al., "Increasing endogenous 2-arachidonoylglycerol levels counteracts colitis and related systemic inflammation" FASEB J. 2011, 25(8):2711-2721.
Antoni et al., "Intestinal barrier in inflammatory bowel disease" in: World Journal of Gastroenterology, 20(5), pp. 1165-1179. Published Feb. 7, 2014.
Azcarate-Peril et al., "The intestinal microbiota, gastrointestinal environment and colorectal cancer: a putative role for probiotics in prevention of colorectal cancer?", American Journal of Physiology, Gastrointestinal and Liver Physiology, Sep. 1, 2011, 304(12): G1055-G1065.

(Continued)

*Primary Examiner* — David J Blanchard
*Assistant Examiner* — Tiffany M Gough
(74) *Attorney, Agent, or Firm* — Lathrop GPM LLP; James H. Velema, Esq.; Judith L. Stone-Hulslander, Esq.

(57) ABSTRACT
The present invention relates to *Akkermansia muciniphila* or fragments thereof for treating a metabolic disorder in a subject in need thereof. The present invention also relates to a composition, a pharmaceutical composition and a medicament comprising *Akkermansia muciniphila* or fragments thereof for treating a metabolic disorder. The present invention also relates to the use of *Akkermansia muciniphila* or fragments thereof for promoting weight loss in a subject in need thereof.

10 Claims, 15 Drawing Sheets

Specification includes a Sequence Listing.

(56)                    References Cited

FOREIGN PATENT DOCUMENTS

| WO | WO 2005/030133 A2 | 4/2005 |
|----|-------------------|--------|
| WO | WO 2006/101244 A2 | 9/2006 |
| WO | WO 2008/073148 A2 | 6/2008 |
| WO | WO 2008/076696 A2 | 6/2008 |
| WO | WO 2008/076696 A3 | 12/2008 |
| WO | WO 2011/137369 A1 | 11/2011 |
| WO | WO 2012/052868 A2 | 5/2012 |
| WO | WO 2012/059499 A1 | 5/2012 |
| WO | WO 2012/059501 A1 | 5/2012 |
| WO | WO 2013/130773 A2 | 9/2013 |
| WO | WO 2014/075745 A1 | 5/2014 |
| WO | WO 2014/076246 A1 | 5/2014 |

OTHER PUBLICATIONS

Bardou et al., "Obesity and colorectal cancer", Gut, 2013, 62: 933-947.

Belzer et al., "Microbes inside—from diversity to function: the case of Akkermansia" ISME J. 2012, 6(8):1449-1458.

Ben-Shabat et al., "An entourage effect: inactive endogenous fatty acid glycerol esters enhance 2-arachidonoyl-glycerol cannabinoid activity" Eur J Pharmacol. 1998, 353(1):23-31.

Berer et al., Commensal microbiota and myelin autoantigen cooperate to trigger autoimmune demyelination, Nature. Oct. 26, 2011;479(7374):538-41.

Cani et al., "Changes in gut microbiota control inflammation in obese mice through a mechanism involving GLP-2-driven improvement of gut permeability" in: Gut, vol. 58, pp. 1091-1103. Published in Feb. 2009.

Cani et al., "Changes in gut microbiota control metabolic endotoxemia-induced inflammation in high-fat diet-induced obesity and diabetes in mice" in: Diabetes, vol. 57, pp. 1470-1481. Published Jun. 2008.

Cani et al., "Metabolic Endotoxemia initiates obesity and insulin resistance" in: Diabetes, vol. 56, pp. 1761-1772. Published Jul. 2007.

Choi et al., "Plasma marker proteins associated with the progression of lung cancer in obese mice fed a high-fat diet", Proteomics, Jun. 2012, 12(12): 1999-2013.

Dabke et al., "The gut microbiome and metabolic syndrome" in: The Journal of Clinical Investigation, vol. 129(10), pp. 4050-4057. Published in Oct. 2019.

Day et al., "Linking inflammation to tumorigenesis in a mouse model of high-fat-diet-enhanced colon cancer", Cytokine, Oct. 2013, 64(1): 454-462.

De Weerth et al., "Crying in infants: on the possible role of intestinal microbiota in the development of colic", Gut Microbes. Sep.-Oct. 2013;4(5):416-21.

De Weerth et al., "Intestinal microbiota of infants with colic: development and specific signatures", Pediatrics. Feb. 2013;131(2):e550-8.

Declaration of Amandine Everard dated Aug. 26, 2022, including Exhibit 1: CV, Exhibit 2: D1 Keystone Poster, and Exhibit 3: Keystone media and communications policy.

Declaration of Patrice Cani dated Aug. 24, 2022, including Exhibit 1-1: CV, Exhibit 1-2: Publication List, Exhibit 2: D1 Keystone Poster, Exhibit 3: Keystone Joint Participant List, and Exhibit 4: 2012 Keystone media and communications policy.

Delzenne et al., "Interaction between obesity and the gut microbiota: relevance in nutrition" Annu. Rev. Nutr. 2011.

Depommier et al., "Supplementation with Akkermansia muciniphila in overweight and obese human volunteers: a proof-of-concept exploratory study" in: Nat Med, vol. 25(7), pp. 1096-1103. Published Jul. 2019.

Derrien et al., "Modulation of Mucosal Immune Response, Tolerance, and Proliferation in Mice Colonized by the Mucin-Degrader Akkermansia muciniphila" Frontiers in Microbiology 2011, 2:166, pp. 1-14.

Derrien et al., "The Mucin degrader Akkermansia muciniphila is an abundant resident of the human intestinal tract" Applied and Environmental Microbiology 2008, 74, 1646-1648.

Derrien et al., "*Akkermansia muciniphila* gen. nov., sp. nov., a human intestinal mucin-degrading bacterium" Int. J Sys. Evol. Microbiol. 2004, 54:1469-1476.

Dewulf et al., "Insight into the prebiotic concept: lessons from an exploratory, double blind intervention study with inulin-type fructans in obese women" in: Gut, vol. 62, pp. 1112-1121. Published in Nov. 2012.

Dingemanse et al., "Akkermansia muciniphila and Helicobacter typhlonius modulate intestinal tumor development in mice", Carcinogenesis, 2015, 36(11): 1388-1396.

Dorhout et al., "Oral administration of deuterium-labelled polyamines to sucking rat pups: Luminal uptake, metabolic fate and effects on gastrointestinal maturation", British Journal of Nutrition, Nov. 1997, pp. 639-654.

Endo et al., "Involvement of JNK pathway in the promotion of the early stage of colorectal carcinogenesis under high-fat dietary conditions", Gut, Dec. 2009, 58(12): 1637-1643, Epublished Jun. 30, 2009.

European Examination Report for European Patent Application No. 21189951.3, dated Aug. 16, 2023.

Everard et al., "Akkermansia muciniphilia links gut barrier function with inflammation and metabolic disorders associated with obesity", Poster Presentation, Keystone Symposia: The Microbiome (Q8), Mar. 4-9, 2012.

Everard et al., "Cross-talk between Akkermansia muciniphila and intestinal epithelium controls diet-induced obesity" NAS USA 2013, 110(22):9066-71.

Everard et al., "Diabetes, obesity and gut microbiota", Best Practice & Research Clinical Gastroenterology, 2013, 27, pp. 73-83.

Everard et al., "Responses of gut microbiota and glucose and lipid metabolism to prebiotics in genetic obese and liet-induced leptin-resistant mice" Diabetes, 2011, 60(11):2775-86.

Extended European Search Report and European Search Opinion for European Patent Application No. 21154064.6, dated Jul. 8, 2021.

Extended European Search Report and European Search Opinion for European Patent Application No. 21189951.3, dated Feb. 15, 2022.

Extended European Search Report and European Search Opinion for European Patent Application No. 24216694.0, dated Apr. 23, 2025.

Extended European Search Report and European Search Opinion for European Patent Application No. 24216695.7, dated Apr. 22, 2025.

Extended European Search Report and European Search Opinion for European Patent Application No. 24216696.5, dated Apr. 22, 2025.

Fujii et al., "A murine model for non-alcoholic steatohepatitis showing evidence of association between diabetes and hepatocellular carcinoma", Med Mol Morphol., Sep. 2013, 46(3): 141-152, Epublished Feb. 22, 2013.

Geurts et al., "Altered gut microbiota and endocannabinoid system tone in obese and diabetic leptin-resistant mice: impact on apelin regulation in adipose tissue" Frontiers in Microbiology 2011, 2:149.

Goris et al., "DNA-DNA hybridization values and their relationship to whole-genome sequence similarities", Int J Syst Evol Microbial. Jan. 2007;57(Pt 1):81-91.

Grivennikov et al., "Immunity, Inflammation, and Cancer", Cell, Mar. 19, 2010, 140(6): 883-899.

Hansen et al., "2-0leoyl glycerol is a GPR119 agonist and signals GLP-1 release in humans" J Clin Endocrinol Metab. 2011, 96(9):E1409-17.

Hansen et al., "Early life treatment with vancomycin propagates Akkermansia muciniphila and reduces diabetes incidence in the NOD mouse" Diabetologia, 2012, 55(8):2285-2294.

Harach et al., "Reduction of Alzheimer's disease beta-amyloid pathology in the absence of gut microbiota", arXiv:1509.02273.

Hsiao et al., "Microbiota modulate behavioral and physiological abnormalities associated with neurodevelopmental Disorders", Cell. Dec. 19, 2013;155(7):1451-63.

Hsieh et al., "Lactobacillus salivarius AP-32 and Lactobacillus reuteri GL-104 decrease glycemic levels and attenuate diabetes-

(56) References Cited

OTHER PUBLICATIONS mediated liver and kidney injury in db/db mice", BMJ Open Diabetes Res Care, 2020, 8(1): e001028, ePublished on Apr. 23, 2020.

International Search Report and Written Opinion for PCT/EP2012/073011, mailed Aug. 19, 2013.

International Search Report and Written Opinion for PCT/EP2012/073972, mailed Feb. 10, 2014.

International Search Report and Written Opinion for PCT/EP2016/060033, mailed Jul. 25, 2016.

International Search Report and Written Opinion for PCT/EP2016/071327, mailed Dec. 6, 2016.

Johansson et al. "The two mucus layers of colon are organized by the MUC2 mucin, whereas the outer layer is a legislator of host-microbial interactions" PNAS U.S.A. 2011, 108 Suppl 1:4659-4665.

Kim et al., "In Vitro Culture Conditions for Maintaining a Complex Population of Human Gastrointestinal Tract Microbiota", Journal of Biomedicine and Biotechnology, 2011, Article ID 838040, 10 pages.

Le Roy et al., "Gut microbiota transplantation demonstrates its causal role in the development of type 2 diabetes and fatty liver" J Hepathol. 2012, 56:S21-S44.

Lee et al., "Effect of Meformin on Metabolic Improvement and Gut Microbiota", Appl Environ Microbial, Oct. 2014, fol. 80, No. 19, pp. 5935-5943.

Louis et al., The gut microbiota, bacterial metabolites and colorectal cancer, Nat Rev Microbial. Oct. 2014;12 ;10):661-72.

Lukovac et al., "Differential Modulation by Akkermansia muciniphila and Faecalibacterium prausnitzii of Host Peripheral Lipid Metabolism and Histone Acetylation in Mouse Gut Organoids", mBio, Jul./Aug. 2014, vol. 5, No. 4.

Martini et al., "Mend your fences. The epithelial barrier and its relationship with mucosal immunity in inflammatory bowel disease" in: Cellular and Molecular Gastroenterology and Hepatology, vol. 4 (1), pp. 33-46. Published Mar. 2017.

Mccole, "Regulation of epithelial barrier function by the inflammatory bowel disease candidate gene, PTPN2" in Ann N Y Acad Sci., vol. 1257, pp. 108-114. Published Jun. 2012.

Moludi, "Metabolic endotoxemia and cardiovascular disease: A systematic review about potential roles of prebiotics and probiotics" in Clinical and Experimental Pharmacology and Physiology, pp. 1-13. Published 2020.

Muccioli et al., "The endocannabinoid system links gut microbiota to adipogenesis" Molecular Systems Biology 2010, 6:392.

Nylund et al., "Severity of atopic disease inversely correlates with intestinal microbiota diversity and butyrate-producing bacteria", Allergy. Feb. 2015;70(2):241-4.

Ottman et al., "Pili-like proteins of Akkermansia muciniphila modulate host immune responses and gut barrier function", Plos One, Mar. 1, 2017, 18 pages.

Padidar et al., "High-Fat Diet Alters Gene Expression in the Liver and Colon: Links to Increased Development of Aberrant Crypt Foci", Dig Dis Sci., 2012, 57(7): 1866-1874.

Park et al., "Dietary and Genetic Obesity Promote Liver Inflammation and Tumorigenesis by Enhancing IL-6 and TNF Expression", Cell, Jan. 22, 2010, 140(2): 197-208.

Park et al., "Effects of diet-induced obesity on colitis-associated colon tumor formation in A/J mice", International Journal of Obesity, Apr. 19, 2012, 36: 273-280.

Park et al., "A high-fat diet increases angiogenesis, solid tumor growth, and lung metastasis of CT26 colon cancer cells in obesity-resistant BALB/c mice", Mol Carcinog., Nov. 2012, 51(11): 869-880, Epublished Sep. 14, 2011.

Pasteur et al., "Pasteur, the father of microbiology", Published by Jilin People's Publishing House, in Jul. 31, 2011, pp. 57 and 59.

Pott et al., "Innate immune signalling at the intestinal epithelium in homeostasis and disease" EMBO Rep. 2012, 13(8):684-698.

Rajilíc-Stojanović et al., "Phylogenetic analysis of dysbiosis in ulcerative colitis during remission", Inflamm Bowel Dis. Mar. 2013;19(3):481-8.

Rajilíc-Stojanović et al., "The first 1000 cultured species of the human gastrointestinal microbiota", FEMS Microbial Rev. 2014, 38(5): 996-1047.

Reunanen et al., "Akkermansia muciniphila Adheres to Enterocytes and Strengthens the Integrity of the Epithelial Sell Layer", Appl Environ Microbial. Jun. 2015;81(11):3655-62.

Reunanen et al., "Characterization of the SpaCBA Pilus Fibers in the Probiotic Lactobacillus rhamnosus GG", Applied and Environmental Microbiology, Apr. 2012, vol. 78, No. 7, pp. 2337-2344.

Scheperjans et al., "Gut microbiota are related to Parkinson's disease and clinical phenotype", Mov Disord. Mar. 2015;30(3):350-8.

Solanki et al., "Development of Microencapsulation Delivery System for Long-Term Preservation of Probiotics as Biotherapeutics Agent", BioMed Research International, 2013, vol. 2013, No. 620719.

Staley et al., "Classification of prokaryotic organisms: an overview", Krieg NR, Holt JG (eds) Bergey's Manual of Systemic Bacteriology, vol. 1. Baltimore, Williams and Wilkins. 1984: 1-4.

Syngelaki et al., "Metformin versus Placebo in Obese Pregnant Women without Diabetes Mellitus", The New England Journal of Medicine, Feb. 4, 2016, 374(5), pp. 434-443.

Tailford et al., "Discovery of intramolecular trans-sialidases in human gut microbiota suggests novel mechanisms of mucosal adaptation", Nature Communications, 2015, 6:7624.

Tang et al., "Consumption of high-fat diet induces tumor progression and epithelial-mesenchymal transition of colorectal cancer in a mouse xenograzŌ model", J Nutr Biochem., Oct. 2012, 23(10): 1302-1313, Epublished Jan. 4, 2012.

Thompson et al., "Obesity, but not ethanol, promotes tumor incidence and progression in a mouse model of hepatocellular carcinoma in vivo", Surg Endosc., Aug. 2013, 27(8): 2782-2791.

Tlaskalová-Hogenová et al., "The role of gut microbiota (commensal bacteria) and the mucosal barrier in the pathogenesis of inflammatory and autoimmune diseases and cancer: contribution of germ-free and gnotobiotic animal models of human diseases", Cellular & Molecular Immunology, 2011, 8:110-20.

Uniprot, "Uncharacterized protein {ECO:00003131EMBLACD04926.1} Flags:Precursor", Jul. 1, 2008.

Vaishnava et al., "The antibacterial lectin RegIIIgamma promotes the spatial segregation of microbiota and host in the intestine" Science. 2011, 334(6053):255-258.

Van Passel et al., "The genome of Akkermansia muciniphila, a dedicated intestinal mucin degrader, and its use in exploring intestinal metagenomes" PLoS One. 2011, 6(3):e16876.

Vykhovanets et al., "High-fat diet increases NF-KB signaling in the prostate of reporter mice", Prostate, Feb. 1, 2011, 71(2): 147-156.

Wang et al., "Akkermansia muciniphila administration exacerbated the development of colitis-associated colorectal cancer in mice", Journal of Cancer, 2022, 13(1): 124-133.

Wang et al., "Stable colonization of Akkermansia muciniphila educates hostintestinal microecology and immunity to battle against inflammatory intestinal diseases", Experimental & Molecular Medicine, Jan. 4, 2023, 55: 55-68.

Wells, "Homeostasis of the gut barrier and potential biomarkers" in American Journal of Physiol Gastrointest Liver Physial, vol. 312, G171-G193. Published Dec. 2016.

Wlodarska et al., "An integrative view of microbiome-host interactions in inflammatory bowel diseases", Cell Host Microbe. May 13, 2015;17(5):577-91.

Zhao et al., "Akkermansia muciniphila: A potential target and pending issues for oncotherapy", Pharmacological Research, Oct. 2023, 196: 10691, Epublished Sep. 9, 2023.

Zitvogel et al., "Cancer and the gut microbiota: an unexpected link", Sci Transl Med. Jan. 21, 2015;7(271):271ps1.

Zoetendal et al., "High-throughput diversity and functionality analysis of the gastrointestinal tract microbiota" Gut 2008, 57: 1605-1615.

*Cani v. Kaplan* Patent Interference No. 106, 130, Cani Exhibit 1011, PCT International Publication No. WO 2013/130773 A2, published Sep. 6, 2013.

(56) References Cited

OTHER PUBLICATIONS

*Cani* v. *Kaplan* Patent Interference No. 106,130, Cani Exhibit 1050, Certified copy of PCT International Application No. PCT/EP2012/073011, filed Nov. 19, 2012.

*Cani* v. *Kaplan* Patent Interference No. 106,130, Cani Exhibit 1051, U.S. Appl. No. 14/443,829, filed May 19, 2015, including official filing receipt.

*Cani* v. *Kaplan* Patent Interference No. 106,130, Cani Exhibit 1101, Declaration of Patrice Cani Under 37 C.F.R. § 41.202(d), dated Oct. 1, 2020 [Redacted].

*Cani* v. *Kaplan* Patent Interference No. 106,130, Cani Exhibit 1107, Declaration of Lucie Geurts Under 37 C.F.R. § 41.202(d), dated Oct. 1, 2020 [Redacted].

*Cani* v. *Kaplan* Patent Interference No. 106,130, Cani Exhibit 1121, Derrien et al., "*Akkermansia muciniphila* gen. nov., sp. Nov., a human intestinal mucin-degrasing bacterium", International Journal of Systematic and Evolutionary Microbiology, 2004, 54: 1469-1476.

*Cani* v. *Kaplan* Patent Interference No. 106,130, Cani Exhibit 1123, Derrien et al., "Modulation of mucosal immune response, tolerancem and proliferation in mice colonized by the mucin-degrader Akkermansia muciniphila", Frontiers in Microbiology, Aug. 1, 2011, 2(166): 1-14.

*Cani* v. *Kaplan* Patent Interference No. 106,130, Cani Exhibit 1217, Cani Laboratory Final Body Weight and Fat Mass Data, generated prior to Feb. 29, 2012.

*Cani* v. *Kaplan* Patent Interference No. 106,130, Cani Exhibit 1218, Cani Laboratory Necropsy Data and Analysis, generated prior to Feb. 29, 2012.

*Cani* v. *Kaplan* Patent Interference No. 106,130, Cani Exhibit 1221, Everard et al., "Akkermansia muciniphila links gut barrier function with inflammation and metabolic disorders associated with obesity", Poster, Université Catholique de Louvain, generated prior to Feb. 29, 2012.

*Cani* v. *Kaplan* Patent Interference No. 106,130, Kaplan Exhibit 1501, Declaration of Andrew Goodman, Ph.D., dated Jul. 23, 2021.

*Cani* V. *Kaplan* Interference No. 106,130, Kaplan Exhibit 1503, Declaration of Nayak L. Polissar, dated Jul. 23, 2021.

*Cani* V. *Kaplan* Interference No. 106,130, Kaplan Exhibit 1507, Cani Exhibit 1217 as provided to Kaplan Counsel, Cani Laboratory Final Body Weight and Fat Mass Data generated prior to Feb. 29, 2012.

*Cani* V. *Kaplan* Interference No. 106,130, Kaplan Exhibit 1508, Cani Exhibit 1218 as provided to Kaplan Counsel, Cani Laboratory Necropsy Data and Analysis generated prior to Feb. 29, 2012.

*Cani* V. *Kaplan* Interference No. 106,130, Kaplan Exhibit 1509, Amendment and Reply Under 37 C.F.R. § 1.111 in U.S. Appl. No. 14/443,829, dated Apr. 12, 2019.

*Cani* V. *Kaplan* Interference No. 106,130, Kaplan Exhibit 1510, Explanation of Cani et al. Priority Evidence Under 37 C.F.R. § 41.202(d) in U.S. Appl. No. 14/443,829, dated Nov. 30, 2020.

*Cani* V. *Kaplan* Interference No. 106,130, Kaplan Exhibit 1511, Request for Continued Examination and Request for Interference Pursuant to 37 C.F.R. § 41.202 in U.S. Appl. No. 14/443,829, dated Nov. 30, 2020.

*Cani* V. *Kaplan* Interference No. 106,130, Kaplan Exhibit 1512, Tremaroli et al., "Functional interactions between the gut microbiota and host metabolism", Nature, Sep. 13, 2012, 489: 242-249.

*Cani* V. *Kaplan* Interference No. 106,130, Kaplan Exhibit 1513, Cani et al., Involvement of gut microbiota in the development of low-grade inflammation and type-2 diabetes associated with obesity, 3(4): 279-288.

*Cani* V. *Kaplan* Interference No. 106,130, Kaplan Exhibit 1514, PCT International Publication No. WO 2008/076696 A2, published Jun. 26, 2008.

*Cani* V. *Kaplan* Interference No. 106,130, Kaplan Exhibit 1515, U.S. Pat. No. 8,192,733 B2, issued Jun. 5, 2012.

*Cani* V. *Kaplan* Interference No. 106,130, Kaplan Exhibit 1516, U.S. Publication No. 2013/0224155 A1, published Aug. 29, 2013, cited against Cani during prosecution.

*Cani* V. *Kaplan* Interference No. 106,130, Kaplan Exhibit 1517, Turnbaugh et al., "An obesity-associated gut microbiome with increased capacity for energy harvest", Nature, 2007, 444(7122): 1027-1031.

*Cani* V. *Kaplan* Interference No. 106,130, Kaplan Exhibit 1519, Hansen et al., "Early life treatment with vancomycin propagates Akkermansia muciniphila and reduces diabetes incidence in the NOD mouse", Diabetologia, 2012, 55: 2285-2294.

*Cani* V. *Kaplan* Interference No. 106,130, Kaplan Exhibit 1520, Cani, "Gut Microbiota, Obesity and Type-2 Diabetes: Insights into toe Prebiotics", Terzo Congresso Nazionale Della Societa' Italiana Di Nutraceutica—Sinut, Sep. 20-21, 2012.

*Cani* V. *Kaplan* Interference No. 106,130, Kaplan Exhibit 1521, Transcription of Exhibit 1507 by A. Young.

*Cani* V. *Kaplan* Interference No. 106,130, Kaplan Exhibit 1522, Transcription of Exhibit 1508 by A. Young.

English translation of Request for Invalidation of Chinese Patent No. ZL201380070847.0 by petitioner Ranjun Wang, dated Jun. 27, 2020.

Becken et al., "Genotypic and Phenotypic Diversity among Human Isolates of Akkermansia muciniphila", American Society for Microbiology, May/Jun. 2021, vol. 12, Issue 3, e00478-a00421.

Cani, Metabolic Endotoxemia Links Low-Grade Inflammation to Metabolic Diseases, Keystone Conference, Mar. 4-9, 2012, Speaker Abstracts, The Microbiome (Q8 025), Microbiota and Metabolism, p. 173.

Everard et al., "Akkermansia muciniphila link gut barrier function with inflammation and metabolic disorders associated with obesity", Keystone Conference, Mar. 4-9, 2012, The Microbiome (Q8), Poster Session 1, Poster 126, p. 185.

Everard et al., "PO9 «Akkermansia muciniphila> : Une nouvelle bactérie jouant un rôle clé dans la fonction barrière de l'intestin, l'inflammation et les désordres métaboliques associés à l'obésité?", Diabetes & Metabolism, Mar. 2012, vol. 38, Suppl. 2, Page A24, with Machine English translation.

Guo et al., "Different subtype strains of Akkermansia muciniphila abundantly colonize in southern China", Journal of Applied Microbiology, 2015, vol. 120: 452-459.

Karlsson et al., "The Microbiota of the Gut in Preschool Children with Normal and Excessive Body Weight", Obesity, Nov. 2012, vol. 20, No. 11, 2257-2261.

Yang et al., "Beneficial Effects of Newly Isolated Akkermansia muciniphila Strains from the Human Gut on Obesity and Metabolic Dysregulation", Microorganisms, 2020, vol. 8, No. 1413, pp. 1-26.

Statement of Opposition of Strawman Limited Against European Patent No. 2919796, filed Jan. 28, 2022.

D2: Derrien et al., "*Akkermansia muciniphila* gen. nov., sp. Nov., a human intestinal mucin-degrading baterium", Int'l Journ of Systematic and Evolutionary Microbiology, 2004, 54: 1469-1476.

D3: Turnbaugh et al., "An obesity-associated gut microbiome with increased capacity for energy harvest", Nature, Dec. 21, 2006, 444: 1027-1031.

D4: PCT International Publication No. WO 2008/076696 A2, published Jun. 26, 2008, entitled: The Gut Microbiome As A Biomarker And Therapeutic Target For Treating Obesity Or An Obesity Related Disorder.

D5: Hansen et al., "Early life treatment with vancomycin propagates *Akkermansia muciniphila* and reduces diabetes incidence in the NOD mouse", Diabetologia, 2012, 55: 2285-2294.

D6: Derrien et al., "Modulation of mucosal immune response, tolerance, and proliferation in mice colonized by the mucin-degrader *Akkermansia muciniphila*", Frontiers in Microbiology, Aug. 2011, vol. 2, Article 166.

D7: Cani et al., "Involvement of gut microbiota in the development of low-grade inflammation and type 2 diabetes associated with obesity", Gut Microbes Jul./Aug. 2012, 3(4): 279-288.

D8: Tremaroli et al., "Functional Interactions bet/Veen the gut microbiota and host metabolism", Nature, Sep. 13, 2012, 489: 242-249.

D9: Cani et al., "Gut Microbiota, Obesity and Type 2 Diabetes: Insights Into the Prebiotics", Terzo Congresso Nazionale Della Societa Italiana di Nutraceutica—Sinut, Sep. 20-21, 2012.

(56) References Cited

OTHER PUBLICATIONS

D10: U.S. Pat. No. 8,192,733 B2, issued Jun. 5, 2012, entitled: Probiotic Composition Useful For Dietary Augmentation And/Or Combating Disease States And Adverse Physiological Conditions.

A4: Everard et al., "Akkermansia muciniphila link gut barrier function with inflammation and metabolic disorders associated with obesity", Keystone Conference, Mar. 4-9, 2012, The Microbiome (Q8), Poster Session 1, Poster 126, p. 185.

A4-1: Extract Translation of Exhibit A4—Everard et al., "Akkermansia muciniphila link gut barrier function with inflammation and metabolic disorders associated with obesity", Keystone Conference, Mar. 4-9, 2012, The Microbiome (Q8), Poster Session 1, Poster 126, p. 185.

A5: Hansen et al., "Early life treatment with vancomycin propagates *Akkermansia muciniphila* and reduces diabetes incidence in the NOD mouse", Diabetologia, 2012, 55: 2285-2294.

A6: Derrien et al., "Modulation of mucosal immune response, tolerance, and proliferation in mice colonized by the mucin-degrader *Akkermansia muciniphila*", Frontiers in Microbiology, Aug. 2011, vol. 2, Article 166.

A6-1: Extract Translation of Exhibit A6—Derrien et al., "Modulation of mucosal immune response, tolerance, and proliferation in mice colonized by the mucin-degrader *Akkermansia muciniphila*", Frontiers in Microbiology, Aug. 2011, vol. 2, Article 166.

A7: Belzer et al., "Microbes inside-from diversity to function: the case of *Akkermansia*", The ISME Journal, 2012, 6: 1449-1458.

A7-1: Extract Translation of Exhibit A7—Belzer et al., "Microbes inside-from diversity to function: the case of *Akkermansia*", The ISME Journal, 2012, 6: 1449-1458.

A8: Everard et al., "Responses of Gut Microbiota and Glucose and Lipid Metabolism to Prebiotics in Genetic Obese and Diet-Induced Leptin-Resistant Mice", Diabetes, Nov. 2011, 60: 2775-2786.

A8-1: Extract Translation of Exhibit A8—Everard et al., "Responses of Gut Microbiota and Glucose and Lipid Metabolism to Prebiotics in Genetic Obese and Diet-Induced Leptin-Resistant Mice", Diabetes, Nov. 2011, 60: 2775-2786.

A9: Cani et al., "Involvement of gut microbiota in the development of low-grade inflammation and type 2 diabetes associated with obesity", Gut Microbes Jul./Aug. 2012, 3(4): 279-288.

A10: Korean Laid-Open Patent Publication No. 10-2020-0110341, published Oct. 12, 2010.

A10-1: Gist of Exhibit A10—Korean Laid-Open Patent Publication No. 10-2020-0110341, published Oct. 12, 2010.

A11: Liu et al., "*Akkermansia muciniphila* Exerts Strain-Specific Effects on DSS-Induced Ulcerative Colitis in Mice", Frontiers in Cellular and Infection Microbiology, Aug. 4, 2021, vol. 11, Article 698914.

A11-1: Extract Translation of Exhibit A11—Liu et al., "*Akkermansia muciniphila* Exerts Strain-Specific Effects on DSS-Induced Ulcerative Colitis in Mice", Frontiers in Cellular and Infection Microbiology, Aug. 4, 2021, vol. 11, Article 698914.

A12: Guo et al., "Genome sequencing of 39 *Akkermansia muciniphila* isolates reveals its population structure, genomic and functional diversity, and global distribution in mammalian gut microbiotas", BMC Genomics, 2017, 18: 800.

A13: Zhai et al., "Strain-Specific Anti-inflammatory Properties of Two Akkermansia muciniphila Strains on Chronic Colitis in Mice", Frontiers in Cellular and Infection Microbiology, Jul. 5, 2019, vol. 9, Article 239.

A13-1: Extract Translation of Exhibit A13—Zhai et al., "Strain-Specific Anti-inflammatory Properties of Two Akkermansia muciniphila Strains on Chronic Colitis in Mice", Frontiers in Cellular and Infection Microbiology, Jul. 5, 2019, vol. 9, Article 239.

A14: Mcfarland et al., "Strain-Specificity and Disease-Specificity of Probiotic Efficacy: A Systematic Review and Meta-Analysis", Frontiers in Medicine, May 7, 2018, vol. 5, Article 124.

A15: Korean Patent Publication No. 10-1093130, dated Dec. 6, 2011.

A16: Japanese Laid-Open Patent Publication No. 2013-522315, dated Jun. 13, 2013.

A16-1: Extract Translation of Exhibit A16—Japanese Laid-Open Patent Publication No. 2013-522315, dated Jun. 13, 2013.

A17: European Patent Publication No. 2397145, dated Dec. 21, 2011.

A17-1: Extract Translation of Exhibit A17—European Patent Publication No. 2397145, dated Dec. 21, 2011.

A18: U.S. Patent Application Publication No. 2005/0186188 A1, dated Aug. 25, 2005.

A18-1: Extract Translation of Exhibit A18—U.S. Patent Application Publication No. 2005/0186188 A1, dated Aug. 25, 2005.

A19: U.S. Patent Application Publication No. 2009/0274661 A1, dated Nov. 5, 2009.

Third Party Observations against European Patent Application No. 21189951.3, dated May 9, 2023.

Annex 01—Zitvogel et al., "Mouse models in oncoimmunology", Nature Reviews, Cancer, Dec. 2016, 16: 759-773.

Annex 02—Les différents types de cancers—ligue nationale contre le cancer Suisse, Sep. 20, 2022.

Annex 03—Makki, "Diversity of Breast Carcinoma: Histological Subtypes and Clinical Relevance", Clinical Medicine Insights: Pathology, 2015, 8: 23-31.

Oral Proceedings Submission for European Patent Application No. 21189951.3, (EP Publication No. 3967315), dated Oct. 10, 2024.

D18: Newmark et al., "A Western-style diet induces benign and malignant neoplasms in the colon of normal C57BI/6 mice", Carcinogenesis, Nov. 2001, 22(11): 1871-1875.

Minutes of the Oral Proceedings Before the Opposition Division for European Patent Application No. 13792006.2 (Patent No. EP 2919796 B2), dated Mar. 5, 2024.

Notice of Opposition for European Patent Application No. 21154064.8 (EP3862010), dated Feb. 12, 2026, filed on behalf of Societe des Produits Nestle S.A.

D1—Everard et al., "Akkermansia muciniphila link gut barrier function with inflammation and metabolic disorders associated with obesity", Keystone Conference, Mar. 4-9, 2012, The Microbiome (Q8), Poster Session 1, Poster 126, p. 185.

D1a—Everard et al., "Akkermansia muciniphila link gut barrier function with inflammation and metabolic disorders associated with obesity", Keystone Conference, Mar. 4-9, 2012, The Microbiome (Q8), Abstract.

D1b - Minutes from Oral Proceedings of European Patent Application No. 13792006.2, dated Nov. 20, 2003.

D2—WO 2013/130773 A2, Published Sep. 6, 2013, Applicant: Ethicon Endo-Surgery, Inc.

D3—WO 2012/016287 A2, Published Feb. 9, 2012, Applicant: Thomas Julius Borody.

D4—WO 2011/039176 A1, Published Apr. 7, 2011, Applicant: Nestec S.A.

D5—WO 2009/021824 A1, Published Feb. 19, 2009, Applicant: Nestec S.A.

D6—WO 2009/055362 A1, Published Apr. 30, 2009, Applicant: Brenda E. Moore.

D7—US 20100172874 A1, Published Jul. 8, 2010, First Inventor: Turnbaugh et al.

D8—Lahtinen et al., "Probiotic viuability—does it matter?", Microbial Ecology in Health & Disease, 2012, 23: 18567.

D9—FAO/WHO, "Guidelines for the Evaluation of Probiotics in Food", Report of a Joint FAO/WHO Working Group on Drafting Guidelines for the Evaluation of Probiotics in Food, Apr. 30-May 1, 2002, 11 pages.

D10—Ouwerkerk et al., "*Akkermansia glycaniphila* sp. nov., an anaerobic mucin-degrading bacterium isolated from reticulated python faeces", Int'l Journal of Systematic and Evolutionaly Microbiology, 2016, 66(11): 4614-4620.

D11—Derrien et al., "The Mucin degrader Akkermansia muciniphila is an abundant resident of the human intestinal tract" Applied and Environmental Microbiology 2008, 74, 1646-1648.

D12—Belzer et al., "Microbes inside-from diversity to function: the case of Akkermansia", The ISME Journal, 2012, 6: 1449-1458.

D13—Santacruz et al., "Gut microbiota composition is associated with body weight, weight gain and biochemical parameters in pregnant women", British Journal of Nutrition, Mar. 8, 2010, 104(1): 83-92.

(56)                References Cited

OTHER PUBLICATIONS

D14—Everard et al., "Responses of Gut Microbiota and Glucose and Lipid Metabolism to Prebiotics in Genetic Obese and Diet-Induced Leptin-Resistant Mice", Diabetes, Nov. 2011, 60: 2775-2786.

D15—Karlsson et al., "The Microbiota of the Gut in Preschool Children with Normal and Excessive Body Weight", Obesity, Nov. 2012, vol. 20, No. 11, 2257-2261.

D16—Derrien et al., "Modulation of Mucosal Immune Response, Tolerance, and Proliferation in Mice Colonized by the Mucin-Degrader Akkermansia muciniphila" Frontiers in Microbiology Aug. 2011, 2:166, pp. 1-14.

D17—Lee et al., "Handbook of Probiotics and Prebiotics", 2009, pp. 52-75 and 535-544.

D18—Manigandan et al., "Probiotics, prebiotics and synbiotics—a review", Biomedical and Pharmacology Journal, 2012, 5(2): 295.

D19—Zhang et al., "Akkermansia muciniphila supplementation in patients with overweight/obese type 2 diabetes: Efficacy depends on its baseline levels in the gut", Clinical and Translational Report, Mar. 4, 2025, 37(3): 592-605.e6.

Notice of Opposition for European Patent Application No. 21183989.9 (EP3943093), dated Feb. 12, 2026, filed on behalf of Universite Catholique de Louvain.

D1—WO 2014/076246 A1, Published May 22, 2014, Applicant: Université Catholique De Louvain.

D3—WO 2016/177797 A1, Published Nov. 10, 2016, Applicant: Univ Wageningen.

D4—KR 10-2013-0021920 A, Applicant: Postech Acad Ind Found.

D4a—Machine English translation of D4 (KR 10-2013-0021920 A).

D5—WO 2010/130659 A1, Published Nov. 18, 2010, Applicant: Nestec S.A.

D6—Commission Implementing regulation (EU) 2022/168, dated Feb. 8, 2022.

D7—Kang et al., "Extracellular Vesicles Derived from Gut Microbiota, Especially Akkermansia muciniphila, Protect the Progression of Dextran Sulfate Sodium-Induced Colitis", Plos One, Oct. 24, 2013, 8(10): e76520.

D8—WO 2010/124256 A2, Published Oct. 28, 2010, Applicant: California Institute of Technology.

D9—Adams et al., "The probiotic paradox: live and dead cells are biological response modifiers", Nutrition Research reviews, Apr. 20, 2010, 23: 37-46.

D10—Pasteurization: Definition and Methods, IDFA, Jun. 2009.

D11—Rouweler et al., "Heat Process Values F (2nd Ed.) for several Commercial Pasteurization and Sterilization Processes: Overview, Uses, and Restrictions", Jun. 12, 2015, Section 3.

D12—Miles et al., "Applying Continuous-Flow Pasteurization and Sterilization Process", Pharmaceutical Technology, May 1, 2013, 2013 Suppl, Issue 3.

D13—Nout et al., "Fermented foods and food safety", Food Research International, 1994, 27: 291-298.

D14—Patent Proprietor R116 EPC Submissions, dated Oct. 21, 2024, pp. 13-15.

D15—Shi et al., "Role of body mass index and weight change in the risk of cancer: A systematic review and meta-analysis of 66 cohort studies", Journal of Global Health, Mar. 29, 2024, 14: 04067.

D16—Itzkowitz et al., "Inflammation and Cancer IV. Colorectal cancer in inflammatory bowel disease: the role of inflammation", Jul. 2004, 287(1): G7-17.

D17—Belzer et al., "Microbes inside-from diversity to function: the case of Akkermansia", The ISME Journal, 2012, 6: 1449-1458.

D18—Ouwerkerk et al., "Akkermansia glycaniphila sp. nov., an anaerobic mucin-degrading bacterium isolated from reticulated python faeces", Int'l Journal of Systematic and Evolutionaly Microbiology, 2016, 66(11): 4614-4620.

O'Mahony et al., "Irritable Bowel Syndrome and Stress-Related Psychiatric Co-morbidities: Focus on Early Life Stress", Handb Exp Pharmacol., 2017, 239: 219-246.

Opening Brief for Appellees in Appeal No. 2025-1886, filed Jan. 8, 2026.

Reply Brief Brief for Appellants in Appeal No. 2025-1886, filed Mar. 2, 2026.

Fig. 2G
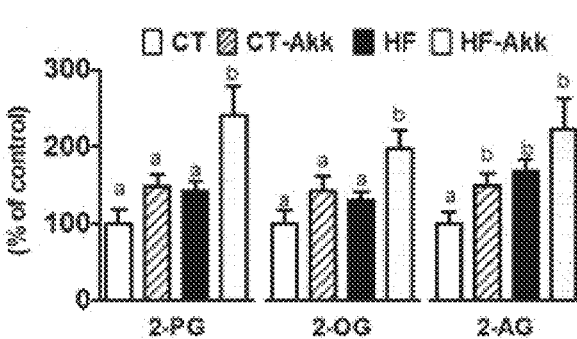
Fig. 2H
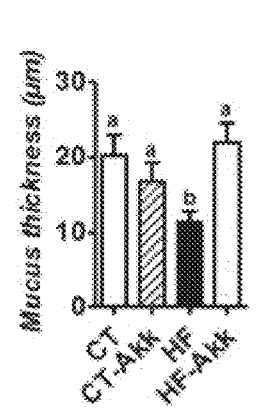
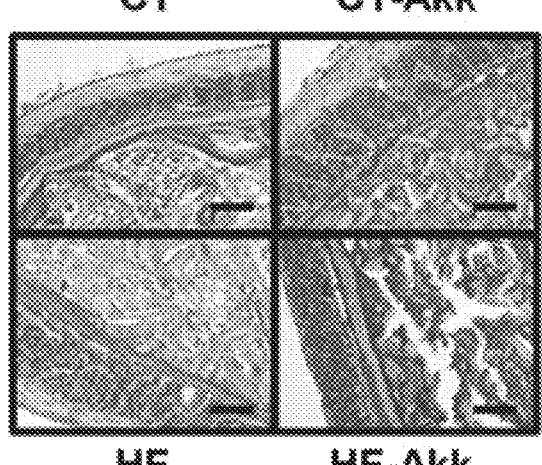
Fig. 2I
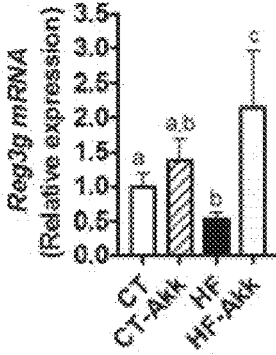

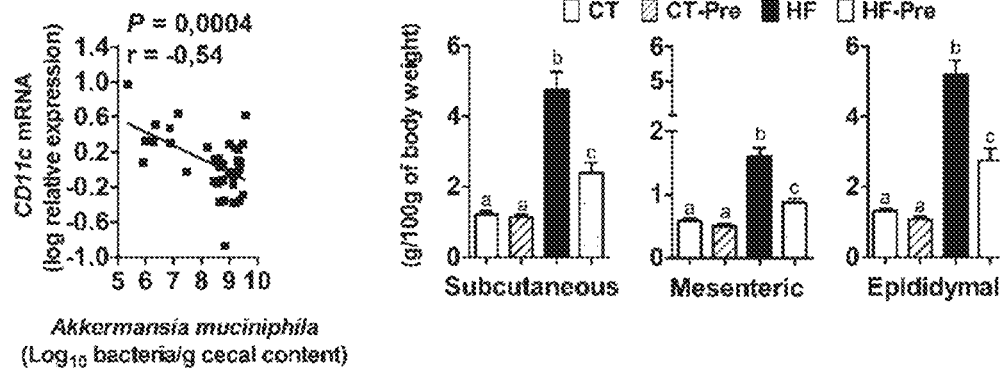
Fig. 3A                              Fig. 3B
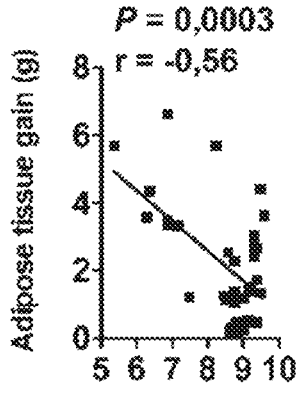
Fig. 3C

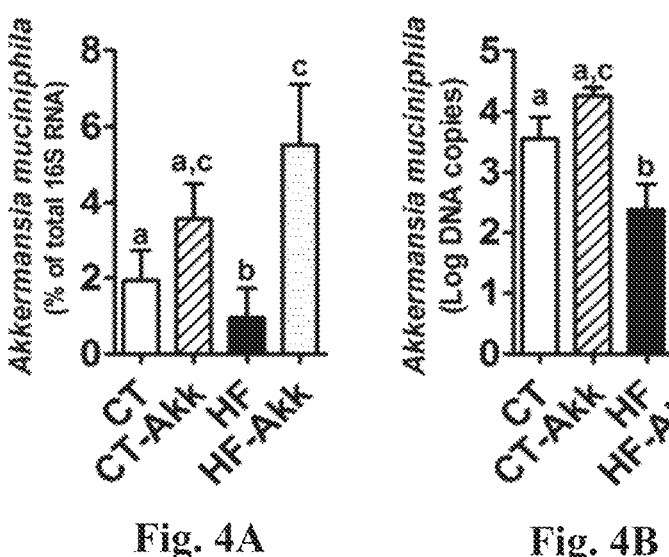
Fig. 4A                    Fig. 4B

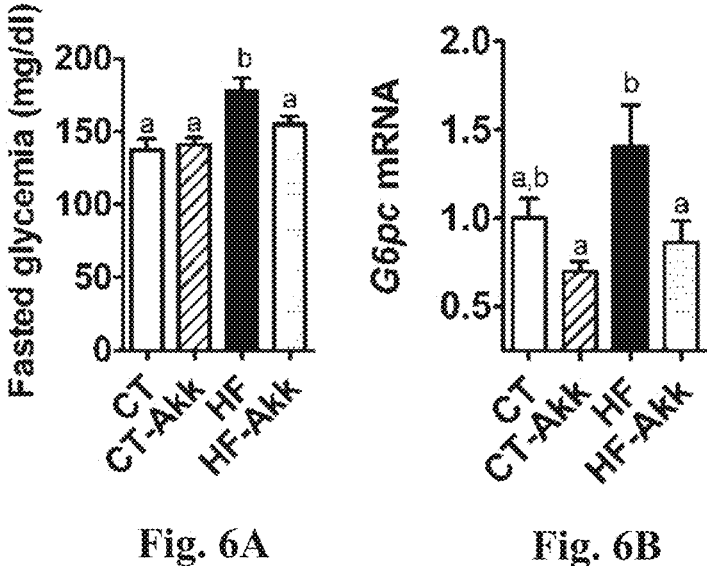
Fig. 6A                    Fig. 6B

Fig. 10A
Fig. 10B
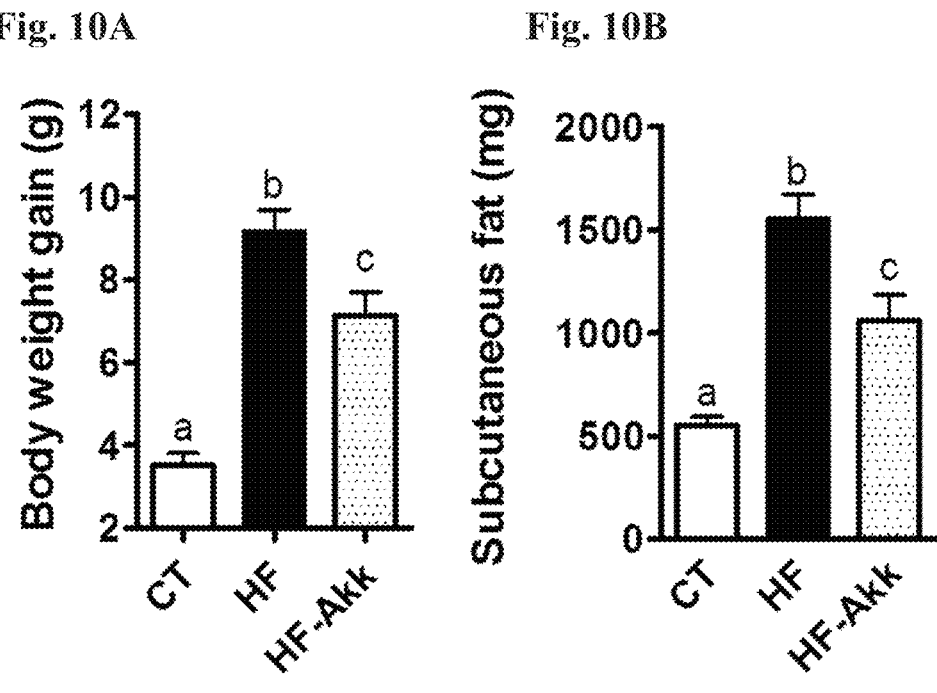
Fig. 10C
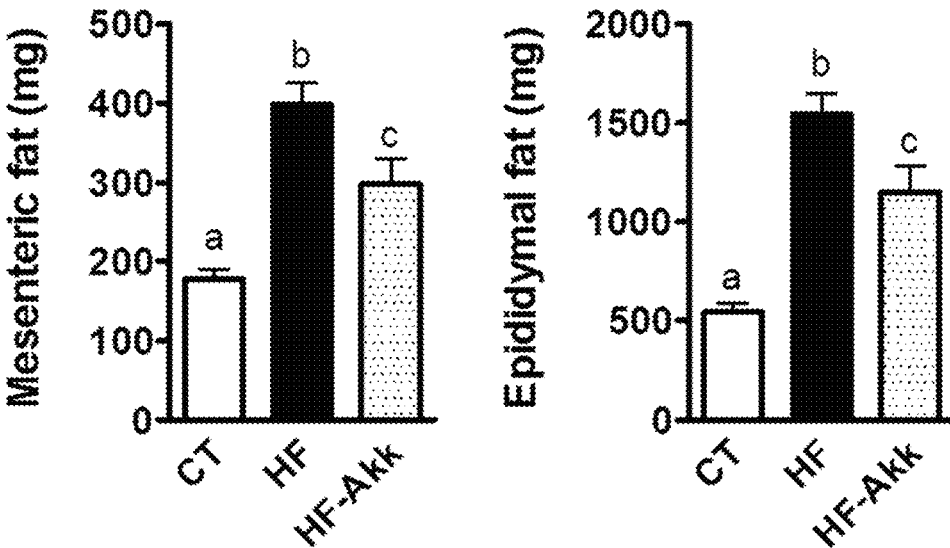

SEQUENCE LISTING

```
Sequence total quantity: 30
SEQ ID NO: 1          moltype = DNA   length = 23
FEATURE               Location/Qualifiers
misc_feature          1..23
                      note = source = /mol_type="unassigned DNA" /note="Primer
                       RPL-19 Forward" /organism="Artificial Sequence"
source                1..23
                      mol_type = other DNA
                      organism = synthetic construct
SEQUENCE: 1
gaaggtcaaa gggaatgtgt tca                                              23
```

-continued

```
SEQ ID NO: 2          moltype = DNA  length = 16
FEATURE               Location/Qualifiers
misc_feature          1..16
                      note = source = /mol_type="unassigned DNA" /note="Primer
                      RPL-19 Reverse" /organism="Artificial Sequence"
source                1..16
                      mol_type = other DNA
                      organism = synthetic construct
SEQUENCE: 2
cctgttgctc acttgt                                                    16

SEQ ID NO: 3          moltype = DNA  length = 21
FEATURE               Location/Qualifiers
misc_feature          1..21
                      note = source = /mol_type="unassigned DNA" /note="Primer
                      Reg3g Forward" /organism="Artificial Sequence"
source                1..21
                      mol_type = other DNA
                      organism = synthetic construct
SEQUENCE: 3
ttcctgtcct ccatgatcaa a                                              21

SEQ ID NO: 4          moltype = DNA  length = 20
FEATURE               Location/Qualifiers
misc_feature          1..20
                      note = source = /mol_type="unassigned DNA" /note="Primer
                      Reg3g Reverse" /organism="Artificial Sequence"
source                1..20
                      mol_type = other DNA
                      organism = synthetic construct
SEQUENCE: 4
catccacctc tgttgggttc                                                20

SEQ ID NO: 5          moltype = DNA  length = 27
FEATURE               Location/Qualifiers
misc_feature          1..27
                      note = source = /mol_type="unassigned DNA" /note="Primer
                      Lyz1 Forward" /organism="Artificial Sequence"
source                1..27
                      mol_type = other DNA
                      organism = synthetic construct
SEQUENCE: 5
gccaaggtct acaatcgttg tgagttg                                        27

SEQ ID NO: 6          moltype = DNA  length = 23
FEATURE               Location/Qualifiers
misc_feature          1..23
                      note = source = /mol_type="unassigned DNA" /note="Primer
                      Lyz1 Reverse" /organism="Artificial Sequence"
source                1..23
                      mol_type = other DNA
                      organism = synthetic construct
SEQUENCE: 6
cagtcagcca gcttgacacc acg                                            23

SEQ ID NO: 7          moltype = DNA  length = 22
FEATURE               Location/Qualifiers
misc_feature          1..22
                      note = source = /mol_type="unassigned DNA" /note="Primer
                      Pla2g2a Forward" /organism="Artificial Sequence"
source                1..22
                      mol_type = other DNA
                      organism = synthetic construct
SEQUENCE: 7
aggattcccc caaggatgcc ac                                             22

SEQ ID NO: 8          moltype = DNA  length = 25
FEATURE               Location/Qualifiers
misc_feature          1..25
                      note = source = /mol_type="unassigned DNA" /note="Primer
                      Pla2g2a Reverse" /organism="Artificial Sequence"
source                1..25
                      mol_type = other DNA
                      organism = synthetic construct
SEQUENCE: 8
cagccgtttc tgacaggagt tctgg                                          25

SEQ ID NO: 9          moltype = DNA  length = 24
```

-continued

```
FEATURE            Location/Qualifiers
misc_feature       1..24
                   note = source = /mol_type="unassigned DNA" /note="Primer
                    CD11cc Forward" /organism="Artificial Sequence"
source             1..24
                   mol_type = other DNA
                   organism = synthetic construct
SEQUENCE: 9
acgtcagtac aaggagatgt tgga                                            24

SEQ ID NO: 10      moltype = DNA  length = 26
FEATURE            Location/Qualifiers
misc_feature       1..26
                   note = source = /mol_type="unassigned DNA" /note="Primer
                    CD11cc Reverse" /organism="Artificial Sequence"
source             1..26
                   mol_type = other DNA
                   organism = synthetic construct
SEQUENCE: 10
atcctattgc agaatgcttc tttacc                                          26

SEQ ID NO: 11      moltype = DNA  length = 26
FEATURE            Location/Qualifiers
misc_feature       1..26
                   note = source = /mol_type="unassigned DNA" /note="Primer
                    Defa Forward" /organism="Artificial Sequence"
source             1..26
                   mol_type = other DNA
                   organism = synthetic construct
SEQUENCE: 11
ggtgatcatc agaccccagc atcagt                                          26

SEQ ID NO: 12      moltype = DNA  length = 24
FEATURE            Location/Qualifiers
misc_feature       1..24
                   note = source = /mol_type="unassigned DNA" /note="Primer
                    Defa Reverse" /organism="Artificial Sequence"
source             1..24
                   mol_type = other DNA
                   organism = synthetic construct
SEQUENCE: 12
aagagactaa aactgaggag cagc                                            24

SEQ ID NO: 13      moltype = DNA  length = 20
FEATURE            Location/Qualifiers
misc_feature       1..20
                   note = source = /mol_type="unassigned DNA" /note="Primer
                    Fasn Forward" /organism="Artificial Sequence"
source             1..20
                   mol_type = other DNA
                   organism = synthetic construct
SEQUENCE: 13
ttccaagacg aaaatgatgc                                                 20

SEQ ID NO: 14      moltype = DNA  length = 20
FEATURE            Location/Qualifiers
misc_feature       1..20
                   note = source = /mol_type="unassigned DNA" /note="Primer
                    Fasn Reverse" /organism="Artificial Sequence"
source             1..20
                   mol_type = other DNA
                   organism = synthetic construct
SEQUENCE: 14
aattgtggga tcaggagagc                                                 20

SEQ ID NO: 15      moltype = DNA  length = 24
FEATURE            Location/Qualifiers
misc_feature       1..24
                   note = source = /mol_type="unassigned DNA" /note="Primer
                    Cpt1a Forward" /organism="Artificial Sequence"
source             1..24
                   mol_type = other DNA
                   organism = synthetic construct
SEQUENCE: 15
agaccgtgag gaactcaaac ctat                                            24
```

-continued

```
SEQ ID NO: 16              moltype = DNA   length = 18
FEATURE                    Location/Qualifiers
misc_feature               1..18
                           note = source = /mol_type="unassigned DNA" /note="Primer
                            Cpt1a Reverse" /organism="Artificial Sequence"
source                     1..18
                           mol_type = other DNA
                           organism = synthetic construct
SEQUENCE: 16
tgaagagtcg ctcccact                                                          18

SEQ ID NO: 17              moltype = DNA   length = 22
FEATURE                    Location/Qualifiers
misc_feature               1..22
                           note = source = /mol_type="unassigned DNA" /note="Primer
                            Pgc1a Forward" /organism="Artificial Sequence"
source                     1..22
                           mol_type = other DNA
                           organism = synthetic construct
SEQUENCE: 17
agccgtgacc actgacaacg ag                                                     22

SEQ ID NO: 18              moltype = DNA   length = 23
FEATURE                    Location/Qualifiers
misc_feature               1..23
                           note = source = /mol_type="unassigned DNA" /note="Primer
                            Pgc1a Reverse" /organism="Artificial Sequence"
source                     1..23
                           mol_type = other DNA
                           organism = synthetic construct
SEQUENCE: 18
gctgcatggt tctgagtgct aag                                                    23

SEQ ID NO: 19              moltype = DNA   length = 19
FEATURE                    Location/Qualifiers
misc_feature               1..19
                           note = source = /mol_type="unassigned DNA" /note="Primer
                            Ppara Forward" /organism="Artificial Sequence"
source                     1..19
                           mol_type = other DNA
                           organism = synthetic construct
SEQUENCE: 19
caacggcgtc gaagacaaa                                                         19

SEQ ID NO: 20              moltype = DNA   length = 19
FEATURE                    Location/Qualifiers
misc_feature               1..19
                           note = source = /mol_type="unassigned DNA" /note="Primer
                            Ppara Reverse" /organism="Artificial Sequence"
source                     1..19
                           mol_type = other DNA
                           organism = synthetic construct
SEQUENCE: 20
tgacggtctc cacggacat                                                         19

SEQ ID NO: 21              moltype = DNA   length = 21
FEATURE                    Location/Qualifiers
misc_feature               1..21
                           note = source = /mol_type="unassigned DNA" /note="Primer
                            Acox1 Forward" /organism="Artificial Sequence"
source                     1..21
                           mol_type = other DNA
                           organism = synthetic construct
SEQUENCE: 21
ctatgggatc agccagaaag g                                                      21

SEQ ID NO: 22              moltype = DNA   length = 21
FEATURE                    Location/Qualifiers
misc_feature               1..21
                           note = source = /mol_type="unassigned DNA" /note="Primer
                            Acox1 Reverse" /organism="Artificial Sequence"
source                     1..21
                           mol_type = other DNA
                           organism = synthetic construct
SEQUENCE: 22
agtcaaaggc atccaccaaa g                                                      21

SEQ ID NO: 23              moltype = DNA   length = 23
```

-continued

```
FEATURE                Location/Qualifiers
misc_feature           1..23
                       note = source = /mol_type="unassigned DNA" /note="Primer
                       Acc1 Forward" /organism="Artificial Sequence"
source                 1..23
                       mol_type = other DNA
                       organism = synthetic construct
SEQUENCE: 23
tgttgagacg ctggtttgta gaa                                                   23

SEQ ID NO: 24          moltype = DNA  length = 25
FEATURE                Location/Qualifiers
misc_feature           1..25
                       note = source = /mol_type="unassigned DNA" /note="Primer
                       Acc1 Reverse" /organism="Artificial Sequence"
source                 1..25
                       mol_type = other DNA
                       organism = synthetic construct
SEQUENCE: 24
ggtccttatt attgtcccag acgta                                                 25

SEQ ID NO: 25          moltype = DNA  length = 21
FEATURE                Location/Qualifiers
misc_feature           1..21
                       note = source = /mol_type="unassigned DNA" /note="Primer
                       Cebpa Forward" /organism="Artificial Sequence"
source                 1..21
                       mol_type = other DNA
                       organism = synthetic construct
SEQUENCE: 25
gagccgagat aaagccaaac a                                                     21

SEQ ID NO: 26          moltype = DNA  length = 16
FEATURE                Location/Qualifiers
misc_feature           1..16
                       note = source = /mol_type="unassigned DNA" /note="Primer
                       Cebpa Reverse" /organism="Artificial Sequence"
source                 1..16
                       mol_type = other DNA
                       organism = synthetic construct
SEQUENCE: 26
gcgcaggcgg tcattg                                                           16

SEQ ID NO: 27          moltype = DNA  length = 20
FEATURE                Location/Qualifiers
misc_feature           1..20
                       note = source = /mol_type="unassigned DNA" /note="Primer
                       G6pc Forward" /organism="Artificial Sequence"
source                 1..20
                       mol_type = other DNA
                       organism = synthetic construct
SEQUENCE: 27
aggaaggatg gaggaaggaa                                                       20

SEQ ID NO: 28          moltype = DNA  length = 20
FEATURE                Location/Qualifiers
misc_feature           1..20
                       note = source = /mol_type="unassigned DNA" /note="Primer
                       G6pc Reverse" /organism="Artificial Sequence"
source                 1..20
                       mol_type = other DNA
                       organism = synthetic construct
SEQUENCE: 28
tggaaccaga tgggaaagag                                                       20

SEQ ID NO: 29          moltype = DNA  length = 20
FEATURE                Location/Qualifiers
misc_feature           1..20
                       note = source = /mol_type="unassigned DNA" /note="Primer
                       F-Akkermansia muciniphila" /organism="Artificial Sequence"
source                 1..20
                       mol_type = other DNA
                       organism = synthetic construct
SEQUENCE: 29
ccttgcggtt ggcttcagat                                                       20
```

-continued

```
SEQ ID NO: 30          moltype = DNA   length = 20
FEATURE                Location/Qualifiers
misc_feature           1..20
                       note = source = /mol_type="unassigned DNA" /note="Primer
                        R-Akkermansia muciniphila" /organism="Artificial Sequence"
source                 1..20
                       mol_type = other DNA
                       organism = synthetic construct
SEQUENCE: 30
cagcacgtga aggtgggggac                                                    20
```

USE OF *AKKERMANSIA* FOR TREATING METABOLIC DISORDERS

RELATED APPLICATIONS

This application is a continuation of U.S. Nonprovisional patent application Ser. No. 14/443,829, filed May 19, 2015, which is a 35 U.S.C. § 371 U.S. national stage entry of International Patent Application No. PCT/EP2013/073972, filed Nov. 15, 2013, which claims priority to PCT/EP2012/073011, filed Nov. 19, 2012.

SEQUENCE LISTING

The instant application contains a Sequence Listing which has been submitted electronically in XML format and is hereby incorporated by reference in its entirety. Said XML file, created on May 30, 2025, is named 766309_AMN9-001USDIV3_ST26. xml and is 42,220 bytes in size.

FIELD OF INVENTION

The present invention relates to the treatment of metabolic disorders, such as, for example, metabolic disorders related to overweight and obesity, such as, for example, Diabetes Mellitus or high cholesterol. The present invention more specifically relates to a composition comprising *Akkermansia* spp or fragments thereof for treating a metabolic disorder.

BACKGROUND OF INVENTION

Obesity is a worldwide problem, with an estimated number of obese adults of about 250 million. This epidemic of obesity is correlated with a great increase in the prevalence of obesity-related disorders, such as, for example, Diabetes, hypertension, cardiac pathologies and liver diseases. Due to these highly disabling pathologies, obesity is currently considered in western countries as one of the most important public health problem. There is thus a real need of compositions and methods for treating or preventing obesity and/or obesity-related disorders.

Obesity and obesity-related diseases are associated with (i) metabolic dysfunctions (with an impact on glucose homeostasis and lipid metabolism for example); (ii) low grade inflammatory state associated to higher blood lipopolysaccharides (LPS) levels (also referred as metabolic endotoxemia); and (iii) impaired gut barrier function (i.e. increased gut permeability). In order to treat obesity, impact on at least one, preferably 2 and more preferably 3 of these 3 factors is thus needed.

The human gut is colonized by a diverse, complex and dynamic community of microbes representing over 1000 different species, which continuously interact with the host (Zoetendal, Rajilic-Stojanovic and de Vos, Gut 2008, 57:1605-1615). The homeostasis of the gut microbiota is dependent on host characteristics (age, gender, genetic background . . . ) and environmental conditions (stress, drugs, gastrointestinal surgery, infectious and toxic agents . . . ), but also on the day-to-day dietary changes. Growing evidences support the role of gut microbiota in the development of obesity and related disorders (Delzenne & Cani, Annu. Rev. Nutr. 2011, 31:15-31).

Therefore, treatment with products that target the gut microbiota appeared as promising therapeutic tools for treating obesity and related disorders. These products may consist of living microbes, such as in the case of most probi-otics, or contain dead microbes or fragments thereof. In addition, these products may comprise substrates that are used by the gut microbiota, such as in the case of prebiotics, or contain compounds that change the balance of the intestinal microbiota, such as specific antimicrobial compounds.

For example, WO 2008/076696 describes the gut microbiota as a therapeutic target for treating obesity and related disorders. WO 2008/076696 specifically describes methods for altering the abundance of Bacteroides and/or Firmicutes in the gut of a subject, by administering antibiotics and/or probiotics to the subject.

Moreover, EP 2 030 623 relates to the prevention and/or treatment of metabolic disorders, such as, for example, obesity related disorders, by regulating the amount of Enterobacteria in the gut. EP 2 030 623 discloses reducing the amount of Enterobacteria in the gut by administering probiotic bacteria, such as, for example, *Bifidobacterium, Lactococcus, Streptococcus, Enterococcus* or *Lactobacillus*.

Furthermore, the Applicant described that the gut microbiota is modified in prebiotic-treated obese mice (Everard et al., Diabetes, 2011 November; 60 (11):2775-86). Moreover, prebiotics (1) improve glucose and lipid metabolisms in obese mice, (2) reduce plasma LPS and improve gut barrier function (e.g. reduction of inflammation) in obese mice, (3) induce an increased enteroendocrine L-cell number in obese mice, and (4) improve leptin sensitivity and glucose homeostasy in diet-induced obese and diabetic mice.

Among the modification induced by prebiotic treatment of obese mice is a considerable alteration of the gut microbiota composition, characterized by (i) a decreased abundance of *Bacteroidetes, Lactobacillus* spp and bacteria of the *Bacteroides-Prevotella* group; and (ii) an increased abundance of *Bifidobacterium* spp., of bacteria of the *E. rectale/C. coccoides* group and of *Akkermansia muciniphila*, belonging to the Verrucomicrobia. *A. muciniphila*, a bacteria firstly identified in 2004 by the Applicant, represents approximately 1 to 3% of the total microbiota of healthy adults (Derrien et al, International Journal of Systematic and Evolutionary Microbiology, 2004, 54:1469-1476; Derrien et al Applied Environmental Microbiology 2008, 74, 1646-1648.).

Indirect evidences suggested a relationship between the abundance of *A. muciniphila* and intestinal dysfunctions or obesity-related disorders. For example, WO 2011/107481 describes that the absence of *Akkermansia muciniphila* in the gut of a subject, combined with the presence of *Bacteroides capillosus* and *Clostridium leptum* indicates that this subject is suffering from ulcerative colitis. Moreover, Hansen and colleagues showed that the administration of an antibiotic, Vancomycin, to neonatal NOD mice (the NOD mouse model is a model for Diabetes) suppresses clinical onset of Diabetes and propagates *Akkermansia muciniphila* (Hansen et al., Diabetologia, 2012 August; 55(8):2285-94). However, this may be an indirect effect due to the insensitivity of intestinal *Akkermansia* spp. to the used antibiotic.

These results thus showed that the complete composition of the gut microbiota is modified following the administration of prebiotic in mice. More specifically, no evidence suggested a specific role of one bacterial species, such as, for example, *Akkermansia muciniphila*, in the beneficial response to prebiotics administration. Moreover, to the Applicant knowledge, no beneficial effect of the direct administration of *Akkermansia muciniphila* has never been described, nor suggested.

Here, the Applicant surprisingly showed that repeated administration of *Akkermansia muciniphila* alone impacts the three underlying dysfunctions associated with obesity and related disorders, i.e. metabolic dysfunctions, low grade inflammatory state associated to higher blood lipopolysaccharides (LPS) levels and impaired gut barrier function. The present invention thus relates to the use of *Akkermansia muciniphila* or fragments thereof for treating obesity and related disorders.

SUMMARY

The present invention thus relates to *Akkermansia muciniphila* or fragments thereof for treating, or for use in treating, a metabolic disorder in a subject in need thereof. In one embodiment of the invention, said metabolic disorder is obesity. In another embodiment of the invention, said metabolic disorder is selected from the group comprising metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system 10 associated with overweight and obesity, cardiovascular diseases, high cholesterol, elevated triglycerides, asthma, sleep apnoea, osteoarthritis, neuro-degeneration, gallbladder disease, syndrome X, inflammatory and immune disorders, atherogenic dyslipidemia and cancer.

The present invention also relates to *Akkermansia muciniphila* or fragments thereof for increasing energy expenditure of a subject, preferably without impacting the food intake of said subject. The present invention also relates to *Akkermansia muciniphila* or fragments thereof for increasing satiety in a subject.

In one embodiment of the invention, viable cells of *Akkermansia muciniphila* are administered to the subject in need thereof.

In one embodiment of the invention, *Akkermansia muciniphila* is orally administered. In one embodiment of the invention, an amount of *Akkermansia muciniphila* ranging from about $1 \cdot 10^2$ to about $1 \cdot 10^{15}$ cfu, preferably from about $1 \cdot 10^4$ to about $1 \cdot 10^{12}$ cfu, more preferably from about $1 \cdot 10^5$ to about $1 \cdot 10^{10}$ cfu, and even more preferably from about $1 \cdot 10^6$ to about $1 \cdot 10^9$ cfu is administered to the subject. In another embodiment of the invention, an amount of *Akkermansia muciniphila* ranging from about $1 \cdot 10^4$ to about $1 \cdot 10^{12}$ cfu, more preferably from about $1 \cdot 10^5$ to about $1 \cdot 10^{11}$ cfu, and even more preferably from about $1 \cdot 10^6$ to about $1 \cdot 10^{10}$ cfu is administered to the subject.

In one embodiment of the invention, *Akkermansia muciniphila* is administered at least once a day. In one embodiment of the invention, *Akkermansia muciniphila* is administered at least three times a week. In another embodiment of the invention, *Akkermansia muciniphila* is administered at least once a week.

In one embodiment of the invention, *Akkermansia muciniphila* is co-administered with another probiotic strain and/or with one or more prebiotics.

Another object of the invention is a composition for treating, or for use in treating, a metabolic disorder, or for increasing energy expenditure or for increasing satiety in a subject comprising *Akkermansia muciniphila* or fragments thereof as described hereinabove in association with an excipient. In one embodiment, said composition is a nutritional composition. In one embodiment of the invention, said composition is orally administered.

The present invention also relates to a pharmaceutical composition for treating, or for use in treating, a metabolic disorder or for increasing energy expenditure or for increasing satiety in a subject comprising *Akkermansia muciniphila* or fragments thereof as hereinabove described in association with a pharmaceutically acceptable vehicle.

Another object of the present invention is a medicament for treating, or for use in treating, a metabolic disorder or for increasing energy expenditure or for increasing satiety in a subject comprising *Akkermansia muciniphila* or fragments thereof as hereinabove described.

Another object of the present invention is the use of *Akkermansia muciniphila* or fragments thereof for promoting weight loss in a subject in need thereof. The present invention also relates to a cosmetic composition comprising *Akkermansia muciniphila* or fragments thereof for promoting weight loss in a subject in need thereof.

Definitions

In the present invention, the following terms have the following meanings:

"Treatment" means preventing (i.e. keeping from happening), reducing or alleviating at least one adverse effect or symptom of a disease, disorder or condition. This term thus refers to both therapeutic treatment and prophylactic or preventative measures; wherein the object is to prevent or slow down (lessen) the targeted pathologic condition or disorder. In one embodiment of the invention, those in need of treatment include those already with the disorder as well as those prone to have the disorder or those in whom the disorder is to be prevented.

"Effective amount" refers to level or amount of agent that is aimed at, without causing significant negative or adverse side effects to the target, (1) delaying or preventing the onset of a metabolic disorder; (2) slowing down or stopping the progression, aggravation, or deterioration of one or more symptoms of the metabolic disorder; (3) bringing about ameliorations of the symptoms of the metabolic disorder; (4) reducing the severity or incidence of the metabolic disorder; (5) curing the metabolic disorder; or (6) restoring the normal amount and/or proportion of *Akkermansia muciniphila* in the gut of the subject to be treated. An effective amount may be administered prior to the onset of a metabolic disorder, for a prophylactic or preventive action. Alternatively or additionally, the effective amount may be administered after initiation of the metabolic disorder, for a therapeutic action.

"*Akkermansia muciniphila*" refers to the strictly anaerobic mucin-degrading bacteria identified by Derrien (Derrien et al, International Journal of Systematic and Evolutionary Microbiology, 2004, 54:1469-1476). Cells are oval-shaped, non-motile and stain Gram-negative. *Akkermansia muciniphila* may also be referred as *Akkermansia* spp. or *Akkermansia*-like bacteria. It belongs to the Chlamydiae/Verrucomicrobia group; Verrucomicrobia phylum. If the taxonomy should change, the skilled artisan would know how to adapt the changes in the taxonomy to deduce the strains that could be used in the present invention. Moreover, the complete genome of *Akkermansia muciniphila* has been determined by the Applicant (van Passel et al, PLoS One 6, 2011: e16876). It is generally accepted that strains with a genome similarity of about 70% can be considered as the same species.

"Probiotics" refers to microbial cell preparations (such as, for example, living microbial cells) or components of microbial cells which, when administered in an effective amount, provide a beneficial effect on the health or well-being of a subject. By definition, all probiotics have a proven non-pathogenic character. In one embodiment, these health benefits are associated with improving the balance of human or animal microbiota in the gastro-intestinal tract, and/or restoring normal microbiota.

"Prebiotic" refers to a substance, such as, for example, a food substance, which may not be digested by humans, but which may be used by bacteria of the gut microbiota and which is intended to promote the growth of probiotic bacteria in the intestine.

"Overweight" refers to a subject situation wherein said subject has a Body Mass Index (BMI) ranging from 25 to 30. As used herein, BMI is defined as the individual's body mass (in kg) divided by the square of his/her height (in meter). "Obesity" refers to a subject situation wherein said subject has a BMI superior or equal to 30.

"Subject" refers to an animal, preferably a mammal, more preferably a human. In one embodiment, the subject is a male. In another embodiment, the subject is a female. In one embodiment of the invention, a subject may also refer to a pet, such as, for example, a dog, a cat, a guinea pig, a hamster, a rat, a mouse, a ferret, a rabbit and the like.

"About" preceding a figure means plus or less 20%, preferably 10% of the value of said figure.

"Fragment" may refer to cellular components, metabolites, secreted molecules and compounds resulting from the metabolism of *Akkermansia muciniphila* and the like. Fragments may be obtained, for example, by recovering the supernatant of a culture of *Akkermansia muciniphila* or by extracting cell components or cell fractions, metabolites or secreted compounds from a culture of *Akkermansia muciniphila*. The term fragment may also refer to a degradation product. A fragment may correspond to a component in the isolated form or to any mixture of one or more components derived from *Akkermansia muciniphila*. In one embodiment, a fragment may correspond to one or more of such a components present in *Akkermansia muciniphila* that is produced in another way, such as using recombinant DNA technology, in a microbial host or in any other (bio)synthetic process.

"Metabolic disorder" refers to disorders, diseases and conditions caused or characterized by abnormal weight gain, energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder may be associated with either a deficiency or an excess in a metabolic pathway resulting in an imbalance in metabolism of carbohydrates, lipids, proteins and/or nucleic acids. Examples of metabolic disorders include, but are not limited to, metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system associated with overweight and obesity, cardiovascular diseases, high cholesterol, elevated triglycerides, asthma, sleep apnoea, osteoarthritis, neuro-degeneration, gallbladder disease, syndrome X, inflammatory and immune disorders, atherogenic dyslipidemia and cancer.

DETAILED DESCRIPTION

This invention relates to *Akkermansia muciniphila* or a fragment thereof for treating, or for use in treating, metabolic disorders in a subject in need thereof.

As used herein, a metabolic disorder is a disorder related to an altered metabolic homeostasis, such as, for example, an altered glucidic or lipidic homeostasis.

In one embodiment of the invention, said metabolic disorder is obesity.

Examples of other metabolic disorders include, but are not limited to, metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system associated with overweight and obesity, cardiovascular diseases, high cholesterol, elevated triglycerides, asthma, sleep apnoea, osteoarthritis, neuro-degeneration, gallbladder disease, syndrome X, inflammatory and immune disorders, atherogenic dyslipidemia and cancer.

In another embodiment, said metabolic disorder is an overweight and/or obesity related metabolic disorder, i.e. a metabolic disorder that may be associated to or caused by overweight and/or obesity. Examples of overweight and/or obesity related metabolic disorder include, but are not limited to metabolic syndrome, insulin-deficiency or insulin-resistance related disorders, Diabetes Mellitus (such as, for example, Type 2 Diabetes), glucose intolerance, abnormal lipid metabolism, atherosclerosis, hypertension, cardiac pathology, stroke, non-alcoholic fatty liver disease, hyperglycemia, hepatic steatosis, dyslipidemia, dysfunction of the immune system associated with overweight and obesity, cardiovascular diseases, high cholesterol, elevated triglycerides, asthma, sleep apnoea, osteoarthritis, neuro-degeneration, gallbladder disease, syndrome X, inflammatory and immune disorders, atherogenic dyslipidemia and cancer.

In one embodiment, said metabolic disorder is Diabetes Mellitus, preferably Type 2 Diabetes. In another embodiment, said metabolic disorder is hypercholesterolemia (also known as high cholesterol). In one embodiment, hypercholesterolemia corresponds to a plasma cholesterol concentration superior or equal to 2 g/L or 5 mmol/L. In another embodiment, hypercholesterolemia corresponds to a ratio plasma concentration of total cholesterol:plasma concentration of HDL (high density lipoprotein cholesterol) superior or equal to 4.5:1, preferably 5:1.

In one embodiment of the invention, living strains of *Akkermansia muciniphila* are used in the present invention, preferably the living strains are derived from cells in stationary phase of growth.

In one embodiment of the invention, *Akkermansia muciniphila* may be in the form of viable cells. In another embodiment of the invention, *Akkermansia muciniphila* may be in the form of non-viable cells.

In one embodiment, metabolically active *Akkermansia muciniphila* cells are used in the present invention. In one embodiment, strains of *Akkermansia muciniphila* are not metabolically inactivated, wherein metabolic inactivation may result, for example, from autoclave treatment.

In one embodiment, *Akkermansia muciniphila* or fragment thereof is substantially purified. As used herein, the term "substantially purified" means that *Akkermansia muciniphila* or fragment thereof is comprised in a sample wherein it represents at least about 50%, preferably at least about 60, 70, 80, 85, 90, 95, 99% or more of the bacterial strains or fragment thereof of said sample.

The present invention also relate to a composition comprising an effective amount of *Akkermansia muciniphila* or a fragment thereof for treating, or for use in treating, a metabolic disorder.

In one embodiment of the invention, the effective amount of *Akkermansia muciniphila* corresponds to the amount of the bacteria sufficient for restoring a normal amount and/or proportion of *Akkermansia muciniphila* within the gut of the subject. Indeed, the Applicant showed that the gut of obese or overweight subject is depleted in *Akkermansia muciniphila* (see Examples). In one embodiment of the invention, the normal amount and/or proportion of *Akkermansia muciniphila* corresponds to the amount, and/or to the proportion of *Akkermansia muciniphila* present in the gut of a healthy subject.

As used herein, the term "healthy subject" is used to define a subject which is not affected by the disease to be treated. For example, if *Akkermansia muciniphila* or a fragment thereof is used for treating obesity, the healthy subject is not affected by obesity. Preferably, the healthy subject shares common characteristics with the subject to be treated, such as, for example, same gender, age, sex, diet, drugs intake or geolocation.

In one embodiment of the invention, the normal proportion of *Akkermansia muciniphila* in the gut ranges from about 0.1% to about 10% (in number of *Akkermansia muciniphila* cells to the total number of bacteria cells of the gut), preferably from about 0.3% to about 5%, more preferably from about 1% to about 3%.

In one embodiment of the invention, the effective amount of *Akkermansia muciniphila* ranges from about $1 \cdot 10^2$ to about $1 \cdot 10^{15}$ cfu, preferably from about $1 \cdot 10^4$ to about $1 \cdot 10^{12}$ cfu, more preferably from about $1 \cdot 10^5$ to about $1 \cdot 10^{10}$ cfu, and even more preferably from about $1 \cdot 10^6$ to about $1 \cdot 10^9$ cfu, wherein cfu stands for "colony forming unit".

In another embodiment of the invention, the effective amount of *Akkermansia muciniphila* ranges from about $1 \cdot 10^6$ to about $1 \cdot 10^{10}$ cfu, preferably from about $1 \cdot 10^8$ to about $1 \cdot 10^{10}$ cfu, more preferably from about $1 \cdot 10^9$ to about $1 \cdot 10^{10}$ cfu.

In another embodiment of the invention, the effective amount of *Akkermansia muciniphila* ranges from about $1 \cdot 10^6$ to about $1 \cdot 10^{10}$ cfu, preferably from about $1 \cdot 10^6$ to about $1 \cdot 10^9$ cfu, more preferably from about $1 \cdot 10^8$ to about $1 \cdot 10^9$ cfu.

In one embodiment of the invention, the effective amount of a fragment of *Akkermansia muciniphila* ranges from fragments derived from about $1 \cdot 10^2$ to about $1 \cdot 10^{15}$ cfu, preferably from about $1 \cdot 10^4$ to about $1 \cdot 10^{12}$ cfu, more preferably from about $1 \cdot 10^5$ to about $1 \cdot 10^{10}$ cfu, and even more preferably from about $1 \cdot 10^6$ to about $1 \cdot 10^9$ cfu, wherein cfu stands for "colony forming unit". In another embodiment of the invention, the effective amount of a fragment of *Akkermansia muciniphila* ranges from fragments derived from about $1 \cdot 10^6$ to about $1 \cdot 10^{10}$ cfu, preferably from about $1 \cdot 10^8$ to about $1 \cdot 10^{10}$ cfu, more preferably from about $1 \cdot 10^9$ to about $1 \cdot 10^{10}$ cfu. In another embodiment of the invention, the effective amount of a fragment of *Akkermansia muciniphila* ranges from fragments derived from about $1 \cdot 10^6$ to about $1 \cdot 10^{10}$ cfu, preferably from about $1 \cdot 10^6$ to about $1 \cdot 10^9$ cfu, more preferably from about $1 \cdot 10^8$ to about $1 \cdot 10^9$ cfu.

In one embodiment of the invention, the composition of the invention comprises an amount of *Akkermansia muciniphila* ranging from about $1 \cdot 10^2$ to about $1 \cdot 10^{15}$ cfu/g of the composition, preferably from about $1 \cdot 10^4$ to about $1 \cdot 10^{12}$ cfu/g of the composition, more preferably from about $1 \cdot 10^5$ to about $1 \cdot 10^{10}$ cfu/g of the composition and even more preferably from about $1 \cdot 10^6$ to about $1 \cdot 10^9$ cfu/g of the composition. In one embodiment of the invention, the composition of the invention comprises an amount of *Akkermansia muciniphila* ranging from about $1 \cdot 10^2$ to about $1 \cdot 10^{15}$ cfu/mL of the composition, preferably from about $1 \cdot 10^4$ to about $1 \cdot 10^{12}$ cfu/mL of the composition, more preferably from about $1 \cdot 10^5$ to about $1 \cdot 10^{10}$ cfu/mL of the composition and even more preferably from about $1 \cdot 10^6$ to about $1 \cdot 10^9$ cfu/mL of the composition. In another embodiment of the invention, the composition of the invention comprises an amount of *Akkermansia muciniphila* ranging from about $1 \cdot 10^6$ to about $1 \cdot 10^{10}$ cfu/g or cfu/mL of the composition, preferably from about $1 \cdot 10^8$ to about $1 \cdot 10^{10}$ cfu/g or cfu/mL, more preferably from about $1 \cdot 10^9$ to about $1 \cdot 10^{10}$ cfu/g or cfu/mL. In another embodiment of the invention, the composition of the invention comprises an amount of *Akkermansia muciniphila* ranging from about $1 \cdot 10^6$ to about $1 \cdot 10^{10}$ cfu/g or cfu/mL of the composition, preferably from about $1 \cdot 10^6$ to about $1 \cdot 10^9$ cfu/g or cfu/mL, more preferably from about $1 \cdot 10^8$ to about $1 \cdot 10^9$ cfu/g or cfu/mL.

In one embodiment of the invention, the composition of the invention comprises an amount of fragments of *Akkermansia muciniphila* ranging from fragments derived from about $1 \cdot 10^2$ to about $1 \cdot 10^{15}$ cfu/g or mL of the composition, preferably from about $1 \cdot 10^4$ to about $1 \cdot 10^{12}$ cfu/g or mL of the composition, more preferably from about $1 \cdot 10^5$ to about $1 \cdot 10^{10}$ cfu/g or mL of the composition and even more preferably from about $1 \cdot 10^6$ to about $1 \cdot 10^9$ cfu/g or mL of the composition. In another embodiment of the invention, the composition of the invention comprises an amount of fragments of *Akkermansia muciniphila* ranging from fragments derived from about $1 \cdot 10^6$ to about $1 \cdot 10^{10}$ cfu/g or cfu/mL of the composition, preferably from about $1 \cdot 10^8$ to about $1 \cdot 10^{10}$ cfu/g or cfu/mL, more preferably from about $1 \cdot 10^9$ to about $1 \cdot 10^{10}$ cfu/g or cfu/mL. In another embodiment of the invention, the composition of the invention comprises an amount of fragments of *Akkermansia muciniphila* ranging from fragments derived from about $1 \cdot 10^6$ to about $1 \cdot 10^{10}$ cfu/g or cfu/mL of the composition, preferably from about $1 \cdot 10^6$ to about $1 \cdot 10^9$ cfu/g or cfu/mL, more preferably from about $1 \cdot 10^8$ to about $1 \cdot 10^9$ cfu/g or cfu/mL.

The present invention also relates to a pharmaceutical composition comprising an effective amount of *Akkermansia muciniphila* or a fragment thereof and at least one pharmaceutically acceptable excipient. In one embodiment of the invention, the pharmaceutical composition of the invention is for treating a metabolic disorder. In another embodiment of the invention, the pharmaceutical composition is for restoring a normal proportion of *Akkermansia muciniphila* in the gut of a subject in need thereof.

As used herein the term "pharmaceutically acceptable excipient" refers to an excipient that does not produce an adverse, allergic or other untoward reaction when administered to an animal, preferably a human. It may include any and all solvents, dispersion media, coatings, isotonic and absorption delaying agents and the like. For human administration, preparations should meet sterility, pyrogenicity, general safety and purity standards as required by FDA Office of Biologics standards.

The present invention also relates to a medicament comprising an effective amount of *Akkermansia muciniphila* or a fragment thereof. In one embodiment of the invention, the medicament of the invention is for treating a metabolic disorder. In another embodiment of the invention, the medicament is for restoring a normal proportion of *Akkermansia muciniphila* in the gut of a subject in need thereof.

The present invention also relates to a method for treating a metabolic disorder in a subject in need thereof, wherein said method comprises administering an effective amount of *Akkermansia muciniphila* or a fragment thereof to the subject.

Another object of the invention is a method for restoring a normal proportion of *Akkermansia muciniphila* in the gut of a subject in need thereof, wherein said method comprises administering an effective amount of *Akkermansia muciniphila* or a fragment thereof to the subject.

In one embodiment, the method of the invention comprises administering an effective amount of the composition, of the pharmaceutical composition or of the medicament of the invention to the subject.

In one embodiment of the invention, *Akkermansia muciniphila* or a fragment thereof, or the composition, pharmaceutical composition or medicament is administered at least once a week, preferably at least twice a week, more preferably at least three times a week, and even more preferably three times a week. In another embodiment, *Akkermansia muciniphila* or a fragment thereof, or the composition, pharmaceutical composition or medicament is administered at least once a day, and preferably at least twice a day.

In one embodiment, *Akkermansia muciniphila* or a fragment thereof, or the composition, pharmaceutical composition or medicament of the invention is administered during 1 week, preferably during 2, 3, 4, 5, 6, 7 or 8 weeks or more.

In one embodiment, *Akkermansia muciniphila* or a fragment thereof, or the composition, pharmaceutical composition or medicament of the invention is administered for a period that lasts until the desired outcome is achieved (e.g. weight loss, metabolic disorder treatment, decrease of cholesterol plasma level . . . ).

In one embodiment, the administration of *Akkermansia muciniphila* or a fragment thereof, or the composition, pharmaceutical composition or medicament of the invention is permanent, i.e. is not limited in time.

In one embodiment of the invention, the daily amount of *Akkermansia muciniphila* administered per day ranges from $1 \cdot 10^2$ to about $1 \cdot 10^{15}$ cfu/day, preferably from about $1 \cdot 10^4$ to about $1 \cdot 10^{12}$ cfu/day, more preferably from about $1 \cdot 10^5$ to about $1 \cdot 10^{10}$ cfu/day and even more preferably from about $1 \cdot 10^6$ to about $1 \cdot 10^9$ cfu/day.

In another embodiment of the invention, the daily amount of *Akkermansia muciniphila* administered per day ranges from $1 \cdot 10^6$ to about $1 \cdot 10^{10}$ cfu/day, preferably from about $1 \cdot 10^8$ to about $1 \cdot 10^{10}$ cfu/day, more preferably from about $1 \cdot 10^9$ to about $1 \cdot 10^{10}$ cfu/day.

In another embodiment of the invention, the daily amount of *Akkermansia muciniphila* administered per day ranges from $1 \cdot 10^6$ to about $1 \cdot 10^{10}$ cfu/day, preferably from about $1 \cdot 10^6$ to about $1 \cdot 10^9$ cfu/day, more preferably from about $1 \cdot 10^8$ to about $1 \cdot 10^9$ cfu/day.

In one embodiment of the invention, the daily amount of fragments of *Akkermansia muciniphila* administered per day ranges from fragments derived from $1 \cdot 10^2$ to about $1 \cdot 10^{15}$ cfu/day, preferably from about $1 \cdot 10^4$ to about $1 \cdot 10^{12}$ cfu/day, more preferably from about $1 \cdot 10^5$ to about $1 \cdot 10^{10}$ cfu/day and even more preferably from about $1 \cdot 10^6$ to about $1 \cdot 10^9$ cfu/day. In another embodiment of the invention, the daily amount of fragments of *Akkermansia muciniphila* administered per day ranges from fragments derived from $1 \cdot 10^6$ to about $1 \cdot 10^{10}$ cfu/day, preferably from about $1 \cdot 10^8$ to about $1 \cdot 10^{10}$ cfu/day, more preferably from about $1 \cdot 10^9$ to about $1 \cdot 10^{10}$ cfu/day. In another embodiment of the invention, the daily amount of fragments of *Akkermansia muciniphila* administered per day ranges from fragments derived from $1 \cdot 10^6$ to about $1 \cdot 10^{10}$ cfu/day, preferably from about $1 \cdot 10^6$ to about $1 \cdot 10^9$ cfu/day, more preferably from about $1 \cdot 10^8$ to about $1 \cdot 10^9$ cfu/day.

In one embodiment of the invention, the subject is overweight. In another embodiment, the subject is obese.

In one embodiment of the invention, the subject is diagnosed with a metabolic disorder, such as, for example, with an overweight and/or obesity related metabolic disorder.

In another embodiment, the subject is at risk of developing a metabolic disorder, such as, for example, an overweight and/or obesity related metabolic disorder. In one embodiment, said risk is related to the fact that the subject is overweight or obese. In another embodiment, said risk corresponds to a predisposition, such as, for example, a familial predisposition to a metabolic disorder, such as, for example, to an overweight and/or obesity related metabolic disorder.

In one embodiment of the invention, the subject presents a deregulation of the gut microbiota composition. Preferably, the gut microbiota of said subject is depleted in *Akkermansia muciniphila* strains. In one embodiment, the proportion of *Akkermansia muciniphila* in the gut of the subject is inferior to 1%, preferably inferior to 0.5%, more preferably inferior to 0.1%, in number of *Akkermansia muciniphila* cells to the total number of bacterial cells in the gut.

The present invention also relates to the cosmetic use of *Akkermansia muciniphila* or a fragment thereof for promoting weight loss in a subject.

Another object of the invention is thus a cosmetic composition comprising a cosmetically effective amount of *Akkermansia muciniphila* or a fragment thereof, and the use thereof for promoting weight loss in a subject. As used herein, a "cosmetically effective amount" refers to the amount of a cosmetic composition necessary and sufficient for promoting a cosmetic effect, such as, for example, for inducing weight loss in a subject.

The present invention also relates to a method for promoting weight loss in a subject in need thereof, wherein said method comprises administering a cosmetically effective amount of *Akkermansia muciniphila* or a fragment thereof to said subject.

In one embodiment, the method of the invention comprises administering a cosmetically effective amount of the composition or of the cosmetic composition of the invention to the subject.

In one embodiment of the invention, the cosmetically effective amount of *Akkermansia muciniphila* ranges from about $1 \cdot 10^2$ to about $1 \cdot 10^{15}$ cfu, preferably from about $1 \cdot 10^4$ to about $1 \cdot 10^{12}$ cfu, more preferably from about $1 \cdot 10^5$ to about $1 \cdot 10^{10}$ cfu and even more preferably from about $1 \cdot 10^6$ to about $1 \cdot 10^9$ cfu. In another embodiment of the invention, the cosmetically effective amount of *Akkermansia muciniphila* ranges from about $1 \cdot 10^6$ to about $1 \cdot 10^{10}$ cfu, preferably from about $1 \cdot 10^8$ to about $1 \cdot 10^{10}$ cfu, more preferably from about $1 \cdot 10^9$ to about $1 \cdot 10^{10}$ cfu. In another embodiment of the invention, the cosmetically effective amount of *Akkermansia muciniphila* ranges from about $1 \cdot 10^6$ to about $1 \cdot 10^{10}$ cfu, preferably from about $1 \cdot 10^6$ to about $1 \cdot 10^9$ cfu, more preferably from about $1 \cdot 10^8$ to about $1 \cdot 10^9$ cfu.

In one embodiment of the invention, the cosmetically effective amount of fragments of *Akkermansia muciniphila* ranges from fragments derived from about $1 \cdot 10^2$ to about $1 \cdot 10^{15}$ cfu, preferably from about $1 \cdot 10^4$ to about $1 \cdot 10^{12}$ cfu, more preferably from about $1 \cdot 10^5$ to about $1 \cdot 10^{10}$ cfu and even more preferably from about $1 \cdot 10^6$ to about $1 \cdot 10^9$ cfu. In another embodiment of the invention, the cosmetically effective amount of fragments of *Akkermansia muciniphila* ranges from fragments derived from about $1 \cdot 10^6$ to about $1 \cdot 10^{10}$ cfu, preferably from about $1 \cdot 10^8$ to about $1 \cdot 10^{10}$ cfu, more preferably from about $1 \cdot 10^9$ to about $1 \cdot 10^{10}$ cfu. In another embodiment of the invention, the cosmetically effective amount of fragments of *Akkermansia muciniphila* ranges from fragments derived from about $1 \cdot 10^6$ to about $1 \cdot 10^{10}$ cfu, preferably from about $1 \cdot 10^6$ to about $1 \cdot 10^9$ cfu, more preferably from about $1 \cdot 10^8$ to about $1 \cdot 10^9$ cfu.

In one embodiment of the invention, *Akkermansia muciniphila* or a fragment thereof, or the composition or cosmetic composition is administered at least once a week, preferably at least twice a week, more preferably at least three times a week, and even more preferably three times a week. In another embodiment, *Akkermansia muciniphila* or a fragment thereof, or the composition or cosmetic composition is administered at least once a day, and preferably at least twice a day.

In one embodiment, *Akkermansia muciniphila* or a fragment thereof, or the composition or cosmetic composition of the invention is administered during 1 week, preferably 2, 3, 4, 5, 6, 7 or 8 weeks or more.

In one embodiment, *Akkermansia muciniphila* or a fragment thereof, or the composition or cosmetic composition of the invention is administered for a period that lasts until the desired outcome is achieved (e.g. weight loss . . . ).

In one embodiment, the administration of *Akkermansia muciniphila* or a fragment thereof, or the composition or cosmetic composition of the invention is permanent, i.e. is not limited in time.

In one embodiment of the invention, the daily amount of *Akkermansia muciniphila* administered per day ranges from $1 \cdot 10^2$ to about $1 \cdot 10^{15}$ cfu/day, preferably from about $1 \cdot 10^5$ to about $1 \cdot 10^{12}$ cfu/day, more preferably from about $1 \cdot 10^8$ to about $1 \cdot 10^{10}$ cfu/day, and even more preferably from about $1 \cdot 10^9$ to about $1 \cdot 10^{10}$ cfu/day. In another embodiment of the invention, the daily amount of *Akkermansia muciniphila* administered per day ranges from $1 \cdot 10^6$ to about $1 \cdot 10^{10}$ cfu/day, preferably from about $1 \cdot 10^8$ to about $1 \cdot 10^{10}$ cfu/day, more preferably from about $1 \cdot 10^9$ to about $1 \cdot 10^{10}$ cfu/day. In another embodiment of the invention, the daily amount of *Akkermansia muciniphila* administered per day ranges from $1 \cdot 10^6$ to about $1 \cdot 10^{10}$ cfu/day, preferably from about $1 \cdot 10^6$ to about $1 \cdot 10^9$ cfu/day, more preferably from about $1 \cdot 10^8$ to about $1 \cdot 10^9$ cfu/day.

In one embodiment of the invention, the daily amount of fragments of *Akkermansia muciniphila* administered per day ranges from fragments derived from about $1 \cdot 10^2$ to about $1 \cdot 10^{15}$ cfu/day, preferably from about $1 \cdot 10^5$ to about $1 \cdot 10^{12}$ cfu/day, more preferably from about $1 \cdot 10^8$ to about $1 \cdot 10^{10}$ cfu/day, and even more preferably from about $1 \cdot 10^9$ to about $1 \cdot 10^{10}$ cfu/day. In another embodiment of the invention, the daily amount of fragments of *Akkermansia muciniphila* administered per day ranges from fragments derived from about $1 \cdot 10^6$ to about $1 \cdot 10^{10}$ cfu/day, preferably from about $1 \cdot 10^8$ to about $1 \cdot 10^{10}$ cfu/day, more preferably from about $1 \cdot 10^9$ to about $1 \cdot 10^{10}$ cfu/day. In another embodiment of the invention, the daily amount of fragments of *Akkermansia muciniphila* administered per day ranges from fragments derived from about $1 \cdot 10^6$ to about $1 \cdot 10^{10}$ cfu/day, preferably from about $1 \cdot 10^6$ to about $1 \cdot 10^9$ cfu/day, more preferably from about $1 \cdot 10^8$ to about $1 \cdot 10^9$ cfu/day.

In one embodiment, said subject is not an obese subject. In another embodiment, said subject is overweight.

In one embodiment of the invention, the composition, the pharmaceutical composition, the cosmetic composition or the medicament further comprises additional probiotic strains or species, such as, for example, bacterial probiotic strains or species; prokaryotes probiotics other than bacteria; or fungal strains or species, preferably yeast strains or species. In one embodiment, said additional probiotic strains or species are selected from those naturally present in the gut of the subject, preferably in the human gut, more preferably in the gut of healthy human subjects.

Examples of bacterial probiotic strains or species that may be used in the present invention include, but are not limited to *Lactobacillus, Lactococcus, Bifidobacterium, Veillonella, Desemzia, Coprococcus, Collinsella, Citrobacter, Turicibacter, Sutterella, Subdoligranulum, Streptococcus, Sporobacter, Sporacetigenium, Ruminococcus, Roseburia, Proteus, Propionobacterium, Leuconostoc, Weissella, Pediococcus, Streptococcus, Prevotella, Parabacteroides, Papillibacter, Oscillospira, Melissococcus, Dorea, Dialister, Clostridium, Cedecea, Catenibacterium, Butyrivibrio, Buttiauxella, Bulleidia, Bilophila, Bacteroides, Anaerovorax, Anaerostopes, Anaerofilum, Enterobacteriaceae, Fermicutes, Atopobium, Alistipes, Acinetobacter, Slackie, Shigella, Shewanella, Serratia, Mahella, Lachnospira, Klebsiella, Idiomarina, Fusobacterium, Faecalibacterium, Eubacterium, Enterococcus, Enterobacter, Eggerthella.*

Examples of prokaryote strains or species that may be used in the present invention include, but are not limited to Archaea, Firmicutes, Bacteroidetes (such as, for example, *Allistipes, Bacteroides ovatus, Bacteroides splachnicus, Bacteroides stercoris, Parabacteroides, Prevotella ruminicola, Porphyromondaceae,* and related genus), Proteobacteria, Betaproteobacteria (such as, for example, *Aquabacterium* and *Burkholderia*), Gammaproteobacteria (such as, for example, *Xanthomonadaceae*), Actinobacteria (such as, for example, *Actinomycetaceae* and *Atopobium*), Fusobacteria, Methanobacteria, Spirochaetes, Fibrobacters, Deferribacteres, *Deinococcus, Thermus,* Cyanobacteria, Methanobrevibacteria, *Peptostreptococcus, Ruminococcus, Coprococcus, Subdolingranulum, Dorea, Bulleidia, Anaerofustis, Gemella, Roseburia, Dialister, Anaerotruncus, Staphylococcus, Micrococcus,* Propionobacteria, Enterobacteriaceae, Faecalibacteria, *Bacteroides, Parabacteroides, Prevotella, Eubacterium,* Bacilli (such as, for example, *Lactobacillus salivarius* and related species, *Aerococcus, Granulicatella, Streptococcus bovis* and related genus and *Streptococcus intermedius* and related genus), *Clostridium* (such as, for example, *Eubacterium hallii, Eubacterium limosum* and related genus) and *Butyrivibrio.*

Examples of fungal probiotic strains or species, preferably yeast probiotic strains or species that may be used in the present invention include, but are not limited *Ascomycetes, Zygomycetes* and *Deuteromycetes,* preferably from the groups *Aspergillus, Torulopsis, Zygosaccharomyces, Hansenula, Candida, Saccharomyces, Clavispora, Bretanomyces, Pichia, Amylomyces, Zygosaccharomyces, Endomycess, Hyphopichia, Zygosaccharomyces, Kluyveromyces, Mucor, Rhizopus, Yarrowia, Endomyces, Debaryomyces,* and/or *Penicillium.*

The Applicant herein shows that the beneficial effects observed after *Akkermansia muciniphila* administration are specific of this bacterial strain. Indeed, it is shown in the Examples that the administration of *Lactobacillus plantarum* WCSF-1 does not have the same beneficial effects.

In one embodiment of the invention, the composition, the pharmaceutical composition, the cosmetic composition or the medicament does not comprise the bacterial strains *Lactobacillus-Enterococcus, Bacteroides* and/or *Atopobium.*

In one embodiment of the invention, the only one microbial strain or species, preferably bacterial strain or species, comprised in the composition, pharmaceutical composition, cosmetic composition or medicament is *Akkermansia muciniphila.*

In one embodiment of the invention, the composition, pharmaceutical composition, cosmetic composition or medicament consists of *Akkermansia muciniphila.*

In another embodiment of the invention, the composition, pharmaceutical composition, cosmetic composition or medicament consists essentially of *Akkermansia muciniphila,* wherein "consisting essentially of" herein means that *Akkermansia muciniphila* is the only microbial strain or species, preferably the only bacterial strain or species comprised in the composition, pharmaceutical composition, cosmetic composition or medicament. In one embodiment of the invention, *Akkermansia muciniphila* or a fragment thereof activates or inhibits the growth and/or biological activity of other bacterial strain(s) or species of the gut microbiota.

In one embodiment of the invention, the composition, the pharmaceutical composition, the cosmetic composition or the medicament further comprises a prebiotic.

Examples of prebiotics that may be used in the present invention include, but are not limited to, inulin and inulin-type fructans, oligofructose, xylose, arabinose, arabinoxylan, ribose, galactose, rhamnose, cellobiose, fructose, lactose, salicin, sucrose, glucose, esculin, tween 80, trehalose, maltose, mannose, mellibiose, mucus or mucins, raffinose, fructooligosaccharides, galacto-oligosaccharides, amino acids, alcohols, and any combinations thereof.

Other non-limiting examples of prebiotics include water-soluble cellulose derivatives, water-insoluble cellulose derivatives, unprocessed oatmeal, metamucil, all-bran, and any combinations thereof.

Examples of water-soluble cellulose derivatives include, but are not limited to, methylcellulose, methyl ethyl cellulose, hydroxyethyl cellulose, ethyl hydroxyethyl cellulose, cationic hydroxyethyl cellulose, hydroxypropyl cellulose, hydroxyethyl methylcellulose, hydroxypropyl methylcellulose, and carboxymethyl cellulose.

*Akkermansia muciniphila* or a fragment thereof or the composition, pharmaceutical composition, cosmetic composition or medicament of the invention may be administered by several routes of administration. Examples of adapted routes of administration include, but are not limited to, oral administration, rectal administration, administration via esophagogastroduodenoscopy, administration via colonoscopy, administration using a nasogastric or orogastric tube and the like.

According to an embodiment, *Akkermansia muciniphila* or a fragment thereof or the composition, pharmaceutical composition, cosmetic composition or medicament of the invention is in a form adapted to oral administration. According to a first embodiment, the form adapted to oral administration is a solid form selected from the group comprising tablets, pills, capsules, soft gelatin capsules, sugarcoated pills, orodispersing/orodispersing tablets, effervescent tablets or other solids. According to a second embodiment, the form adapted to oral administration is a liquid form, such as, for example, a drinkable solution, liposomal forms and the like.

In one embodiment, the composition, pharmaceutical composition, cosmetic composition or medicament of the invention further comprises excipients, diluent and/or carriers selected with regard to the intended route of administration. Examples of excipients, diluent and/or carriers include, but are not limited to, water, phosphate buffer saline, anaerobic phosphate buffer saline, sodium bicarbonate, juice, milk, yogurt, infant formula, dairy product, coloring agents, such as, for example, titane dioxide (E171), iron dioxide (E172) and brilliant black BN (E151); flavoring agents; thickeners, such as, for example, glycerol monostearate; sweeteners; coating agents, such as, for example, refined colza oil, soya oil, peanut oil, soya lecithin or fish gelatin; diluting agents, such as, for example, lactose, monohydrated lactose or starch; binding agents, such as, for example, povidone, pregelatinized starch, gums, saccharose, polyethylene glycol (PEG) 4000 or PEG 6000; disintegrating agents, such as, for example, microcrystalline cellulose or sodium carboxymethyl starch, such as, for example, sodium carboxymethyl starch type A; lubricant agents, such as, for example, magnesium stearate; flow agent, such as, for example, colloidal anhydrous silica, etc.

In one embodiment of the invention, the composition, pharmaceutical composition, cosmetic composition or medicament is in the form of a nutritional composition, i.e. comprises liquid or solid food, feed or drinking water. In one embodiment of the invention, the composition, pharmaceutical composition, cosmetic composition or medicament is a food product, such as, for example, dairy products, dairy drinks, yogurt, fruit or vegetable juice or concentrate thereof, powders, malt or soy or cereal based beverages, breakfast cereal such as muesli flakes, fruit and vegetable juice powders, cereal and/or chocolate bars, confectionary, spreads, flours, milk, smoothies, confectionary, milk product, milk powder, reconstituted milk, cultured milk, yoghurt, drinking yoghurt, set yoghurt, drink, dairy drink, milk drink, chocolate, gels, ice creams, cereals, reconstituted fruit products, snack bars, food bars, muesli bars, spreads, sauces, dips, dairy products including yoghurts and cheeses, drinks including dairy and non-dairy based drinks, sports supplements including dairy and non-dairy based sports supplements.

In one embodiment of the invention, the composition, pharmaceutical composition, cosmetic composition or medicament is in the form of a food additive, drink additive, dietary supplement, nutritional product, medical food or nutraceutical composition.

*Akkermansia muciniphila* is a strictly anaerobic bacterium. Therefore, in the embodiment where viable or living strains are used, prolonged contact with oxygen should be avoided. Examples of means for avoiding prolonged contact with oxygen include, but are not limited to, freeze of the bacterial cells or packaging in a sealed container and the like.

The Applicant herein showed that obesity and related disorders are associated with an increased gut permeability and with impaired mucus production, epithelium barrier, immune system and/or antibacterial compounds production by the subject; and that the administration of *A. muciniphila* may restore these parameters.

Therefore, the present invention also relates to *Akkermansia muciniphila* or a fragment thereof for decreasing gut permeability and/or for restoring impaired mucus production and/or for restoring epithelium barrier and/or for restoring immune system and/or for decreasing the production of antibacterial compounds. Another object of the invention is a method for decreasing gut permeability and/or for restoring impaired mucus production and/or for restoring epithelium barrier and/or for restoring immune system and/or for decreasing the production of antibacterial compounds in a subject in need thereof, comprising administering an effective or cosmetically effective amount of *Akkermansia muciniphila* or a fragment thereof to a subject in need thereof.

The Applicant surprisingly showed that the administration of *A. muciniphila* controls gut barrier by regulating mucus layer thickness and the production of colon antimicrobial peptides (such as, for example, RegIIIgamma). In addition, they also showed that *A. muciniphila* regulates the production of acylglycerols that belongs to the endocannabinoids family involved in the control of inflammation, gut barrier and gut peptides secretion (GLP-1 and GLP-2). GLP-1 and GLP-2 are involved in a great variety of functions, including improving insulin signalling, decreasing inflammation, and promoting satiety.

Therefore, the present invention also relates to *Akkermansia muciniphila* or a fragment thereof for controlling gut barrier function, and to a method for controlling gut barrier function comprising administering an effective or cosmetically effective amount of *Akkermansia muciniphila* or a fragment thereof to a subject in need thereof. In one embodiment, *Akkermansia muciniphila* or a fragment thereof regulates mucus layer thickness (which may be decreased in obesity or other metabolic disorders). In another embodiment, the administration of *Akkermansia muciniphila* or a fragment thereof induces the production of colon antimicrobial peptides, such as, for example, RegIIIgamma. In another embodiment, the administration of *Akkermansia muciniphila* or a fragment thereof induces the production of compounds of the endocannabinoids family, such as, for example, acylglycerols selected from the group comprising 2-oleoylglycerol, 2-palmitoylglycerol and 2-arachidonoylglycerol. In another embodiment, the administration of *Akkermansia muciniphila* or a fragment thereof regulates mucus turnover.

Another object of the invention concerns *Akkermansia muciniphila* or a fragment thereof for use in treating metabolic dysfunction associated with or caused by a metabolic disorder. Still another object of the invention is thus a method for treating metabolic dysfunction associated with or caused by a metabolic disorder in a subject in need thereof, comprising administering an effective amount or a cosmetically effective amount of *Akkermansia muciniphila* or a fragment thereof to a subject in need thereof.

The Applicant also showed that the administration of *Akkermansia muciniphila* controls fat storage and adipose tissue metabolism. Therefore, another object of the invention concerns *Akkermansia muciniphila* or a fragment thereof for use in controlling fat storage and adipose tissue metabolism. Another object of the invention is also a method for controlling fat storage and adipose tissue metabolism comprising administering an effective amount or a cosmetically effective amount of *Akkermansia muciniphila* or a fragment thereof to a subject in need thereof. In one embodiment, said control does not involve any change in food intakes. In one embodiment of the invention, administration of *Akkermansia muciniphila* or a fragment thereof abolishes metabolic endotoxemia. In another embodiment, administration of *Akkermansia muciniphila* or a fragment thereof lowers fat mass. In another embodiment, administration of *Akkermansia muciniphila* or a fragment thereof increases mRNA expression of adipocyte differentiation and lipid oxidation, preferably without affecting lipogenesis.

The Applicant also showed that the administration of *Akkermansia muciniphila* regulates adipose tissue metabolism and glucose homeostasis. The present invention thus relates to *Akkermansia muciniphila* or a fragment thereof for use in the regulation of adipose tissue metabolism and glucose homeostasis; and to a method for regulating adipose tissue metabolism and glucose homeostasis comprising administering an effective amount or a cosmetically effective amount of *Akkermansia muciniphila* or a fragment thereof to a subject in need thereof. In one embodiment of the invention, the administration of *Akkermansia muciniphila* or a fragment thereof reverses diet-induced fasting hyperglycemia. In another embodiment, the administration of *Akkermansia muciniphila* or a fragment thereof induces a reduction of at least 10%, preferably of at least 30%, more preferably of at least 40% of hepatic glucose-6-phosphatase expression. In another embodiment, the administration of *Akkermansia muciniphila* or a fragment thereof induces a reduction of the insulin-resistance index. In one embodiment, said reduction of the insulin-resistance index is of at least 5%, preferably of at least 10%, more preferably of at least 15%.

Moreover, the Applicant showed that the administration of *Akkermansia muciniphila* leads to the normalization of adipose tissue CD11c subpopulation of macrophages. The amount of cells of this population of macrophages is increased in metabolic disorders such as, for example, obesity and Type 2 Diabetes, and is a hallmark of inflammation related to these metabolic disorders. Therefore, the present invention also relates to *Akkermansia muciniphila* or a fragment thereof for treating inflammation, preferably low grade inflammation, associated with or caused by metabolic disorders; and to a method for treating inflammation related to metabolic disorders comprising administering an effective amount or a cosmetically effective amount of *Akkermansia muciniphila* or a fragment thereof to a subject in need thereof. In one embodiment of the invention, the administration of *Akkermansia muciniphila* or a fragment thereof decreases the amount of CD11c macrophages in the adipose tissue.

Finally, the Applicant showed that the administration of *Akkermansia muciniphila* decreases plasma cholesterol in high-fat diet fed mice. Therefore, the present invention also relates to *Akkermansia muciniphila* or a fragment thereof for decreasing plasma cholesterol; and to a method for decreasing plasma cholesterol comprising administering an effective amount or a cosmetically effective amount of *Akkermansia muciniphila* or a fragment thereof to a subject in need thereof.

In one embodiment of the invention, the administration of *Akkermansia muciniphila* or a fragment thereof to a subject has no impact on food intake of said subject.

In one embodiment of the invention, the administration of *Akkermansia muciniphila* or a fragment thereof to a subject increases energy expenditure of said subject, preferably without impacting the food intake of said subject.

The present invention thus also relates to a method of increasing energy expenditure of a subject, comprising administering *Akkermansia muciniphila* or a fragment thereof, or a composition, pharmaceutical composition, cosmetic composition or medicament of the invention to the subject, preferably in a therapeutically or cosmetically effective amount. Preferably, the method of the invention does not comprise or further comprise modulating the food intake of said subject. In one embodiment of the invention, the method of the invention increases energy expenditure, thereby inducing durable weight loss in the subject, and thereby treating metabolic disorders in said subject, such as, for example, obesity related metabolic disorders.

In one embodiment, the administration of *Akkermansia muciniphila* or a fragment thereof to a subject increases satiety in said subject. Consequently, according to this embodiment, the method of the invention increases satiety in a subject, thereby inducing durable weight loss in the subject, and thereby treating metabolic disorders in said subject, such as, for example, obesity related metabolic disorders.

BRIEF DESCRIPTION OF THE DRAWINGS

(FIG. 1A) *Akkermansia muciniphila* abundance ($Log_{10}$ of bacteria/g of cecal content) measured in the cecal content of leptin-deficient (ob-ob) obese mice (n=5) and their lean littermates (lean) (n=5). (FIG. 1B) *Akkermansia muciniphila* abundance ($Log_{10}$ of bacteria/g of cecal content) measured in the cecal content of obese mice fed a normal chow diet (ob-CT) or treated with prebiotics (ob-Pre) for 5-weeks (n=10). (FIG. 1C) *Akkermansia muciniphila* abundance (Logo of bacteria per g of cecal content) measured in the cecal content of control diet-fed mice (CT) or CT diet-fed mice treated with prebiotics (CT-Pre) added in tap water and HF diet-fed mice (HF) or HF diet-fed mice treated with prebiotics (HF-Pre) added in tap water for 8-weeks (n=10). (FIG. 1D) Portal vein serum LPS levels (n=7-9).

(FIG. 2A) PCA analysis based on MITChip phylogenetic fingerprints of the gut microbiota from the cecal contents of control groups (CT and HF) and *Akkermansia muciniphila* treated groups (CTA and HFA). (FIG. 2B) Portal vein serum LPS levels (n=6-10). (FIG. 2C) Total fat mass gain measured by time-domain nuclear magnetic resonance (n=10). (FIG. 2D) Insulin resistance index was determined by multiplying the area under the curve (from 0 min to 15 min) of both blood glucose and plasma insulin obtained following an oral glucose load (2 g of glucose per kg of body weight) performed after 4 weeks of treatment (n=10). (FIG. 2E) Adipose tissue macrophages infiltration marker CD11c mRNA (n=10). (FIG. 2F) Adipocyte differentiation (CCAAT/enhancer—binding protein-α, encoded by Cebpa), lipogenesis (acetyl-CoA carboxylase, encoded by Acc1; fatty acid synthase, encoded by Fasn) and lipid oxidation (carnitine palmitoyltransferase-1, encoded

Figure 1A:
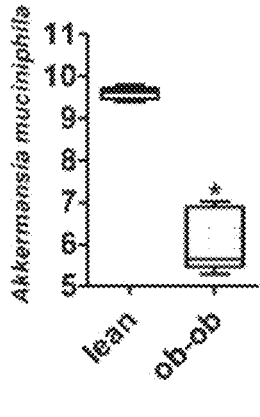
FIGS. 1A-1D are a combination of graphs showing that *Akkermansia muciniphila* abundance is decreased in obese and diabetic mice, whereas prebiotic treatment restores it to basal levels and improves metabolic endotoxemia and related disorders.

18 by Cpt1; acyl-CoA-oxidase encoded by Acox1; peroxisome proliferator-activated receptor gamma coactivator, encoded by Pgc1a; and peroxisome proliferator-activated receptor alpha, encoded by Ppara) markers mRNA expression were measured in the visceral fat depots (mesenteric fat) (n=10). (FIG. 2G) Ileum 2-palmitoylglycerol (2-PG), 2-oloeylglycerol (2-OG), 2-arachidonoylglycerol (2-AG) (expressed as % of the control) (n=10). (FIG. 2H) Mucus layer thickness measured by histological analyses following alcian blue staining. Representative alcian blue images used for the mucus layer thickness measurements, bars=40 µm (n=7-8). (FIG. 2I) Colon regenerating islet-derived 3-gamma (RegIIIγ, encoded by Reg3 g) mRNA expression (n=10). Data in FIG. 2A-2I have been obtained in the same group of mice. Data in FIGS. 2B-2I are shown as mean±s.e.m. Data with different superscript letters are significantly different (P<0.05), according to the post-hoc ANOVA one-way statistical analysis.

FIGS. 3A-3C are a combination of graphs and pictures showing that prebiotic-treated mice exhibited inverse relationship between *Akkermansia muciniphila* and adipose tissue macrophage infiltration or fat mass gain. (FIG. 3A) Pearson's correlation between adipose tissue CD11c mRNA levels and *Akkermansia muciniphila* abundance ($Log_{10}$ of bacteria per g of cecal content) measured in the cecal content of control diet-fed mice (CT) or CT diet-fed mice treated with prebiotics (CT-Pre) added in tap water and HF diet-fed mice (HF) or HF diet-fed mice treated with prebiotics (HF-Pre) added in tap water for 8-weeks, inset indicates Pearson's correlation coefficient (r) and the corresponding P value. (FIG. 3B) Subcutaneous, mesenteric and epididymal fat depots weight (g per 100 g of body weight) (n=10). (FIG. 3C) Pearson's correlation between adipose tissue mass gain and cecal content *Akkermansia muciniphila* abundance ($Log_{10}$ of bacteria per g of cecal content), inset indicates Pearson's correlation coefficient (r) and the corresponding P value. Data in FIGS. 3A-3C have been obtained in the same group of mice, and are shown as mean±s.e.m. Data with different superscript letters are significantly different (P<0.05), according to the post-hoc ANOVA one-way statistical analysis.

FIGS. 4A-4B are a combination of graphs showing that daily oral gavage with *Akkermansia muciniphila* increases cecal abundance of these bacteria. *Akkermansia muciniphila* abundance expressed as (FIG. 4A) % of total 16S RNA or (FIG. 4B) $Log_{10}$ DNA copies measured in mice treated by daily oral gavage with *Akkermansia muciniphila* ($2\cdot10^8$ bacterial cells suspended in 200 µl sterile anaerobic phosphate buffer saline (PBS)) and fed a control diet (CT-Akk) or a HF-diet (HF-Akk) compared to mice fed a control diet (CT) or a high-fat diet (HF) and treated by daily oral gavage with an equivalent volume of sterile anaerobic PBS for 4-weeks (n=10).

FIGS. 5A-5D are a combination of graphs and pictures showing that *Akkermansia muciniphila* treatment reduces fat mass without affecting food intake. (FIG. 5A) Subcutaneous, mesenteric and epididymal fat depots weight (g per 100 g of body weight) of mice treated by daily oral gavage with *Akkermansia muciniphila* ($2\cdot10^8$ bacterial cells suspended in 200 µl sterile anaerobic phosphate buffer saline (PBS)) and fed a control diet (CT-Akk) or a HF-diet (HF-Akk) or mice fed a control diet (CT) or a high-fat diet (HF) and treated by daily oral gavage with an equivalent volume of sterile anaerobic PBS for 4-weeks (n=10). (FIG. 5B) Cumulative food intake (g) over the 4-weeks of treatment. (FIG. 5C) Final body weight (n=10). (FIG. 5D) Final fat and lean mass expressed in percentage of final body weight and measured using 7.5 MHz time-domain NMR (LF50 minispec; Bruker, n=10). Data are shown as mean±s.e.m. Data with different superscript letters are significantly different (P<0.05), according to the post-hoc ANOVA one-way statistical analysis.

FIGS. 6A-6B are a combination of graphs showing that *Akkermansia muciniphila* treatment normalizes fasted glycemia and reduces fasted hepatic G6pc mRNA expression. (FIG. 6A) Fasted glycemia measured in mice treated by daily oral gavage with *Akkermansia muciniphila* $(2 \cdot 10^8$ bacterial cells suspended in 200 µl sterile anaerobic phosphate buffer saline (PBS)) and fed a control diet (CT-Akk) or a HF-diet (HF-Akk) or mice fed a control diet (CT) or a high-fat diet (HF) and treated by daily oral gavage with an equivalent volume of sterile anaerobic PBS for 4-weeks (n=10). (FIG. 6B) Glucose-6 phosphatase (encoded by G6pc) mRNA expression levels measured in the liver at the end of the 4-weeks period (n=10). Data are shown as mean±s.e.m. Data with different superscript letters are significantly different (P<0.05), according to the post-hoc ANOVA one-way statistical analysis.

FIGS. 7A-7E is a combination of graphs showing that *Akkermansia muciniphila* treatment has minor effects on antibacterial peptides content in the ileum and IgA levels in the faeces. Antibacterial peptides mRNA expression of (FIG. 7A) Regenerating islet-derived 3-gamma (RegIIIγ, encoded by Reg3g), (FIG. 7B) Phospholipase A2 group IIA (encoded by Pla2g2a), (FIG. 7C) α-defensins (encoded by Defa) and (FIG. 7D) Lysozyme C (encoded by Lyz1) measured in the ileum of mice treated by daily oral gavage with *Akkermansia muciniphila* $(2 \cdot 10^8$ bacterial cells suspended in 200 µl sterile anaerobic phosphate buffer saline (PBS)) and fed a control diet (CT-Akk) or a HF-diet (HF-Akk) or mice fed a control diet (CT) or a high-fat diet (HF) and treated by daily oral gavage with an equivalent volume of sterile anaerobic PBS for 4-weeks (n=10). (FIG. 7E) Fecal IgA levels (µg/g of feces). Data are shown as mean±s.e.m. Data with different superscript letters are significantly different (P<0.05), according to the post-hoc ANOVA one-way statistical analysis.

FIGS. 8A-8G are a combination of histograms, graphs and images showing that heat-inactivated *A. muciniphila* did not counteract metabolic endotoxemia, diet-induced obesity, oral glucose intolerance, did not improve adipose tissue metabolism and gut barrier function in diet-induced obese mice. Control mice were fed a control (CT) or HF diet (HF) and treated with a daily oral gavage containing sterile anaerobic PBS and glycerol for 4 weeks daily. Treated mice received an oral gavage of alive *A. muciniphila* (HF-Akk) or metabolically inactivated *A. muciniphila* (HF-K-Akk) $(2 \cdot 10^8$ bacterial cells suspended in 200 µl of sterile anaerobic phosphate-buffered saline (PBS)) and fed a HF diet (n=8). (FIG. 8A) Portal vein serum LPS levels (n=6-7). (FIG. 8B) Total fat mass gain measured by time-domain nuclear magnetic resonance (n=7-8). (FIG. 8C) Plasma glucose profile following 2 g/kg glucose oral challenge in freely moving mice, and the histogram in (FIG. 8D) shows the mean area under the curve (AUC) measured between 0 and 120 min after glucose load (n=7-8). (FIG. 8E) mRNA expression of markers of adipocyte differentiation (Cebpa), lipogenesis (Acc1; Fasn) and lipid oxidation (Cpt1; Acox1; Pgc1a; and Ppara) was measured in visceral fat depots (mesenteric fat) (n=8). (FIG. 8F) Thickness of the mucus layer measured by histological analyses following alcian blue staining (CT n=4, HF n=6, HF-Akk and HF-K-Akk n=5). (FIG. 8G) Representative alcian blue images that were used for mucus layer thickness measurements, bars=40 µm. M=mucosa, IM=inner mucus layer. Data are shown as mean±s.e.m. Data with different superscript letters are significantly different (P<0.05) according to post-hoc ANOVA one-way statistical analysis.

Figure 9A:
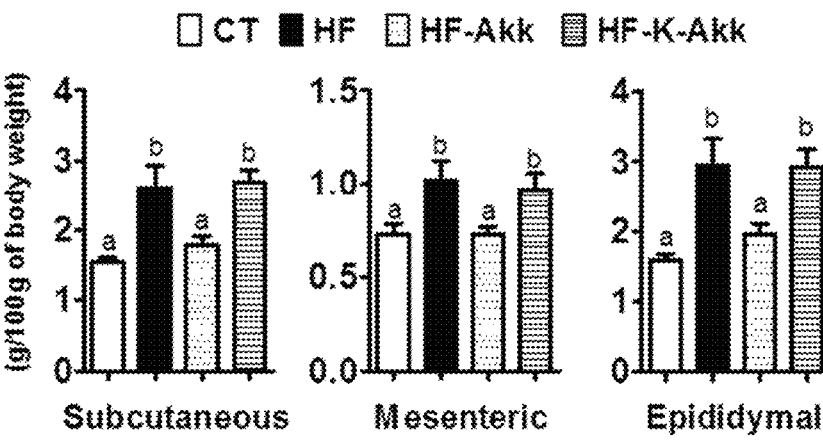
Figure 9B:
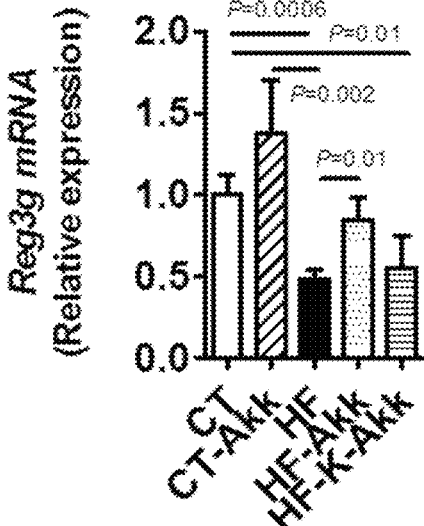

FIGS. 9A-9B is a combination of histograms showing that heat-inactivated *A. muciniphila* did not reduce subcutaneous, mesenteric and epididymal fat mass and did not increase colon antimicrobial peptides in mice on an HF diet. (FIG. 9A) Subcutaneous, mesenteric and epididymal fat depot weights (g per 100 g body weight) measured in control mice fed a control (CT) or HF diet (HF) and treated with a daily oral gavage containing sterile anaerobic PBS and glycerol for 4 weeks daily. Treated mice received an oral gavage of alive *A. muciniphila* (HF-Akk) or killed *A. muciniphila* (HF-K-Akk) $(2 \cdot 10^8$ bacterial cells suspended in 200 µl of sterile anaerobic PBS) and fed a HF diet (n=8). (FIG. 9B) mRNA expression of colon regenerating islet-derived 3-gamma (RegIIIγ, encoded by Reg3g) mRNA expression (n=8-18), data represents the results from the two *A. muciniphila* studies. Data are shown as mean±s.e.m. Data with different superscript letters are significantly different (P<0.05) according to a post-hoc ANOVA one-way statistical analysis.

FIGS. 10A-10C are a combination of histograms showing the efficiency of a treatment with *A. muciniphila* 3 times a week during 8 weeks. (FIG. 10A) Body weight (g) measured in control mice fed a control (CT) (n=8) or HF diet (HF) (n=10) and treated 3 times per weeks by oral gavage with sterile anaerobic PBS containing glycerol or *A. muciniphila* (HF-Akk) (n=10) for 8 weeks. $(2 \cdot 10^8$ bacterial cells suspended in 200 µl of sterile anaerobic PBS). (FIG. 8B) Subcutaneous fat mass. (FIG. 10C) Visceral adipose tissues (mesenteric and epidydimal). Data are shown as mean±s.e.m. Data with different superscript letters are significantly different (P<0.05) according to a post-hoc ANOVA one-way statistical analysis.

Figure 11:
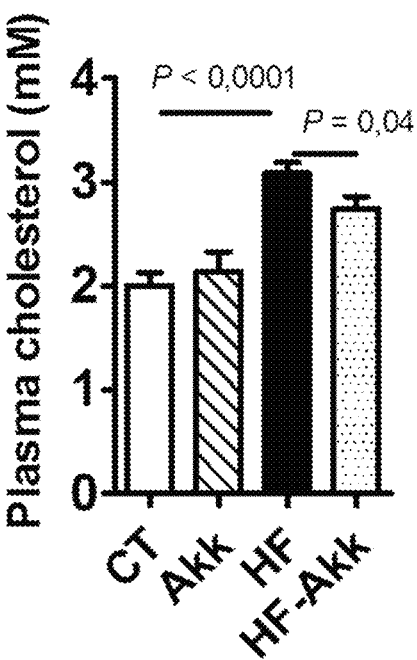
Figures 12A, 12B, 12C, 12D, 12E:
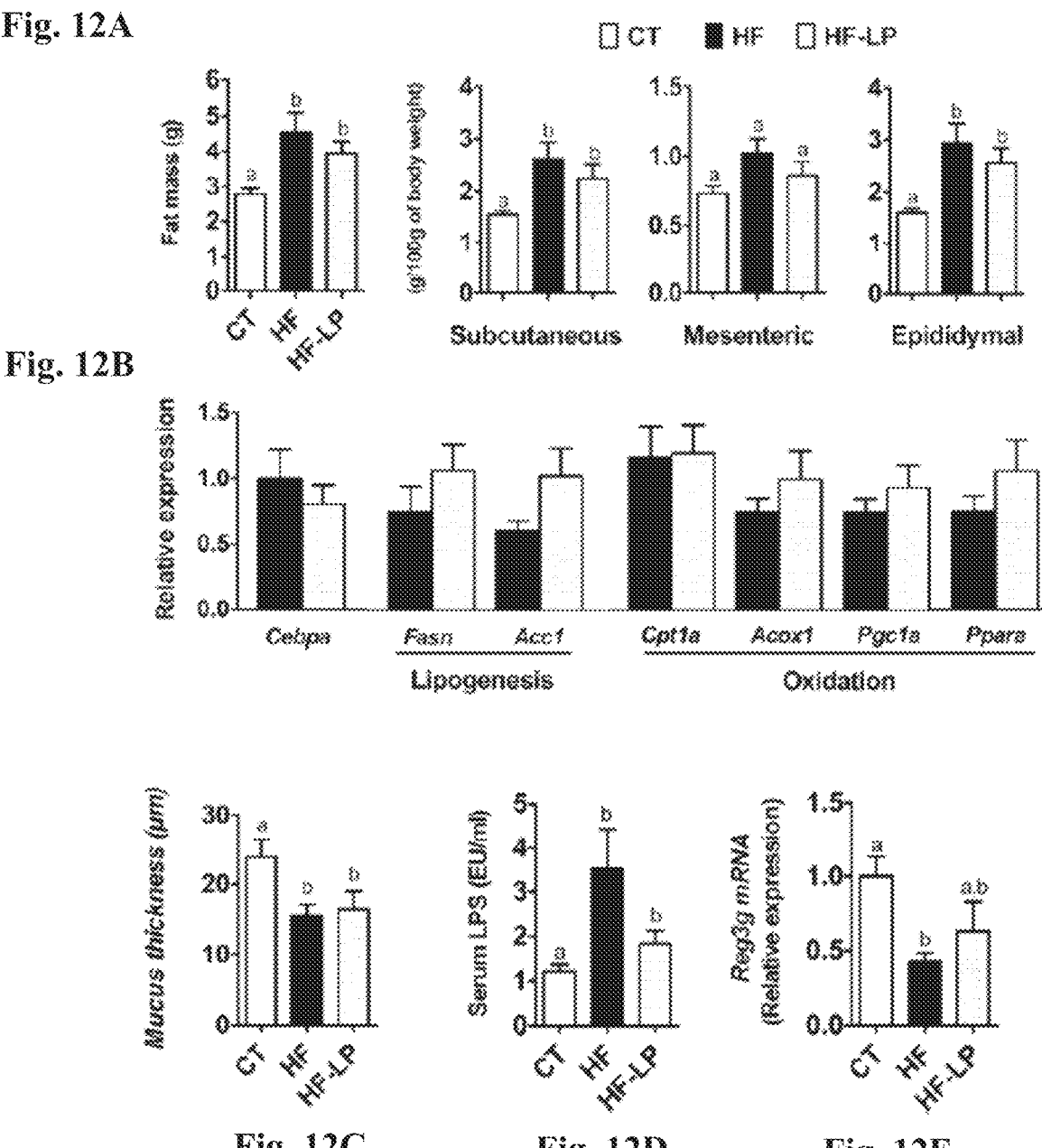

FIG. 11 is an histogram showing that *A. muciniphila* reduces plasma cholesterol in mice fed a high-fat diet. (CT) Mice fed a control diet; (Akk) Mice treated by daily oral gavage with *Akkermansia muciniphila* $(2 \cdot 10^8$ bacterial cells suspended in 200 µl sterile anaerobic phosphate buffer saline (PBS)) and fed a control diet; (HF) Mice fed a high-fat diet; (HF-Akk) Mice treated by daily oral gavage with *Akkermansia muciniphila* $(10^9$ bacterial cells suspended in 200 µl sterile anaerobic phosphate buffer saline (PBS)) and fed a HF-diet.

FIGS. 12A-12E are a combination of histograms showing that *L. plantarum* WCFS1 did not reduce fat mass and did not improve adipose tissue metabolism and gut barrier function in diet-induced obese mice. Control mice were fed a control (CT) or HF diet (HF) and treated with a daily oral gavage containing sterile anaerobic PBS and glycerol for 4 weeks. Treated mice received an oral gavage of *L. plantarum* WCFS1 (HF-LP) $(2 \cdot 10^8$ bacterial cells suspended in 200 µL of sterile anaerobic PBS) and fed a HF diet (n=7-8). (FIG. 12A) Final fat mass measured by time-domain NMR (n=7-8). s.c., mesenteric and epididymal fat depot weights (g/100 g of body weight) (n=7-8). (FIG. 12B) mRNA expression of markers of adipocyte differentiation (Cebpa), lipogenesis (Acc1; Fasn) and lipid oxidation (Cpt1; Acox1; Pgc1a; and Ppara) was measured in visceral fat depots (mesenteric fat) (n=7-8). (FIG. 12C) Thickness of the mucus layer measured by histological analyses after alcian blue staining (n=4-6). (FIG. 12D) Portal vein serum LPS levels (n=6-7). (FIG. 12E) mRNA expression of colon RegIIIγ (encoded by Reg3g) mRNA expression (n=8-18). Data are shown as mean±s.e.m. Data with different superscript letters are significantly different (P<0.05) according to post hoc ANOVA one-way statistical analysis.

EXAMPLES

The present invention is further illustrated by the following examples.

Materials and Methods

Mice ob/ob experiment: ob/ob versus lean study: Six-week-old ob/ob (n=5/group) mice (C57BL/6 background, Jackson-Laboratory, Bar Harbor, ME, USA) were housed in a controlled environment (12-h daylight cycle, lights-off at 6-pm) in groups of two or three mice/cage, with free access to food and water. The mice were fed a control diet (A04, Villemoisson-sur-orge, France) for 16 weeks. Cecal content was harvested immersed in liquid nitrogen, and stored at −80° C., for further *Akkermansia muciniphila* analysis.

ob/ob prebiotic study: Six-week-old ob/ob (n=10/group) mice (C57BL/6 background, Jackson-Laboratory, Bar Harbor, ME, USA) were housed in a controlled environment (12-h daylight cycle, lights-off at 6-pm) in groups of two mice/cage, with free access to food and water. The mice were fed a control diet (Ob-CT) (A04, Villemoisson-sur-Orge, France) or a control diet supplemented with prebiotics, such as oligofructose (Ob-Pre) (Orafti, Tienen, Belgium) for 5-weeks as previously described (Everard et al. Diabetes 60, 2775-2786 (2011)). This set of mice has been previously characterized in Everard et al (Everard et al. Diabetes 60, 2775-2786 (2011)).

High-Fat prebiotic experiment: A set of 10-week-old C57BL/6J mice (40 mice, n=10/group) (Charles River, Brussels, Belgium) were housed in groups of five mice/cage, with free access to food and water. The mice were fed a control diet (CT) (A04, Villemoisson-sur-orge, France) or a control diet and treated with prebiotics, such as oligofructose (Orafti, Tienen, Belgium) (0.3 g/mouse/day) added in tap water (CT-Pre), or fed a high-fat diet (HF) (60% fat and 20% carbohydrates (kcal/100 g), D12492, Research diet, New Brunswick, NJ, USA) or a HF diet and treated with oligofructose (0.3 g/mouse/day) added in tap water (HF-Pre). Treatment continued for 8 weeks.

HFD *Akkermansia muciniphila* treatment: A set of 10-week-old C57BL/6J mice (40 mice, n=10/group) (Charles River, Brussels, Belgium) were housed in groups of 2 mice/cage, with free access to food and water. The mice were fed a control diet (CT) (AIN93Mi; Research diet, New Brunswick, NJ, USA) or a high-fat diet (HF) (60% fat and 20% carbohydrates (kcal/100 g), D12492, Research diet, New Brunswick, NJ, USA). Mice were treated with an oral administration of *Akkermansia muciniphila* by oral gavage at the dose $2 \cdot 10^8$ cfu/0.2 ml suspended in sterile anaerobic phosphate buffer saline (CT-Akk and HF-Akk) and control groups were treated with an oral gavage of an equivalent volume of sterile anaerobic phosphate buffer saline (CT and HF). Treatment continued for 4 weeks.

*A. muciniphila* Muc$^T$ (ATTC BAA-835) was grown anaerobically in a mucin-based basal medium as previously described (Derrien et al Int J Syst Evol Microbiol 54, 1469-1476 (2004)) and then washed and suspended in anaerobic phosphate buffer saline, including 25% (v/v) glycerol, to an end concentration of $1 \cdot 10^{10}$ cfu/ml.

HFD *Akkermansia muciniphila* alive treatment vs heat-killed and *Lactobacillus platarum* WCFS1: A set of 10-week-old C57BL/6J mice (40 mice, n=8/group) (Charles River, Brussels, Belgium) were housed in groups of 2 mice/cage, with free access to food and water. The mice were fed a control diet (CT) (AIN93Mi; Research diet, New Brunswick, NJ, USA) or a high-fat diet (HF) (60% fat and 20% carbohydrates (kcal/100 g), D12492, Research diet, New Brunswick, NJ, USA). Mice were treated daily with an oral administration of *Akkermansia muciniphila* by oral gavage at the dose $2 \cdot 10^8$ cfu/0.2 ml suspended in sterile anaerobic phosphate buffer saline *A. muciniphila* was heat-killed/inactivated by autoclaving (15 min, 121° C., 225 kPa). A viability check by culturing on mucin-containing medium confirmed the absence of any viable cells. *Lactobacillus plantarum* WCFS1 was grown anaerobically in MRS medium (Difco Lactobacilli MRS broth; BD), washed, concentrated, and manipulated an identical ways as the *A. muciniphila* preparation. The two controls group (CT and HF) were treated daily with an oral gavage of an equivalent volume of sterile anaerobic PBS containing a similar end concentration of glycerol (2.5%) (reduced with one drop of 100 mM titanium citrate) as the treatment groups for 4 weeks.

Food and water intake were recorded once a week. Body composition was assessed by using 7.5 MHz time domain-nuclear magnetic resonance (TD-NMR) (LF50 minispec, Bruker, Rheinstetten, Germany).

All mouse experiments were approved by and performed in accordance with the guidelines of the local ethics committee. Housing conditions were specified by the Belgian Law of Apr. 6, 2010, regarding the protection of laboratory animals (agreement number LA1230314).

Tissue Sampling

The animals have been anesthetized with isoflurane (Forene®, Abbott, Queenborough, Kent, England) before exsanguination and tissue sampling, then mice were killed by cervical dislocation. Adipose depots (epididymal, subcutaneous and mesenteric), liver were precisely dissected and weighed; the addition of the three adipose tissues corresponds to the adiposity index. The intestinal segments (ileum, cecum and colon), the cecal content and the adipose tissues were immersed in liquid nitrogen, and stored at −80° C., for further analysis.

Mucus Layer Thickness

Proximal colon segments were immediately removed and fixed in Carnoy's solution (ethanol-acetic acid-chloroform, 6/3/1 v/v/v) for two hours at 4° C. Then the samples were immersed in ethanol 100% for 24 hours prior to processing for paraffin embedding. Paraffin sections of 5 μm were stained with alcian blue. A minimum of 20 different measurements were made perpendicular to the inner mucus layer per field by an investigator blinded to the experimental groups. 5 to 19 randomly selected fields were analyzed for each colon for a total of 2146 measurements by using an image analyzer (Motic-image Plus 2.0 ML, Motic, China).

RNA Preparation and Real-Time qPCR Analysis

Total RNA was prepared from tissues using TriPure reagent (Roche). Quantification and integrity analysis of total RNA was performed by running 1 μl of each sample on an Agilent 2100 Bioanalyzer (Agilent RNA 6000 Nano Kit, Agilent).

cDNA was prepared by reverse transcription of 1 μg total RNA using a Reverse Transcription System kit (Promega, Leiden, The Netherlands). Real-time PCRs were performed with the StepOnePlus™ real-time PCR system and software (Applied Biosystems, Den Ijssel, The Netherlands) using Mesa Fast qPCR™ (Eurogentec, Seraing, Belgium) for detection according to the manufacturer's instructions. RPL19 was chosen as the housekeeping gene. All samples were run in duplicate in a single 96-well reaction plate, and data were analyzed according to the 2-ACT method. The identity and purity of the amplified product was checked through analysis of the melting curve carried out at the end of amplification. Primer sequences for the targeted mouse genes are presented in the Table 1 below.

| Primers | | Sequence |
|---------|---------|----------|
| RPL-19 | Forward | GAAGGTCAAAGGGAATGTGTTCA (SEQ ID NO: 1) |
| | Reverse | CCTGTTGCTCACTTGT (SEQ ID NO: 2) |
| Reg3g | Forward | TTCCTGTCCTCCATGATCAAA (SEQ ID NO: 3) |
| | Reverse | CATCCACCTCTGTTGGGTTC (SEQ ID NO: 4) |
| Lyz1 | Forward | GCCAAGGTCTACAATCGTTGTGAGTTG (SEQ ID NO: 5) |
| | Reverse | CAGTCAGCCAGCTTGACACCACG (SEQ ID NO: 6) |
| Pla2g2a | Forward | AGGATTCCCCCAAGGATGCCAC (SEQ ID NO: 7) |
| | Reverse | CAGCCGTTTCTGACAGGAGTTCTGG (SEQ ID NO: 8) |
| CD11cc | Forward | ACGTCAGTACAAGGAGATGTTGGA (SEQ ID NO: 9) |
| | Reverse | ATCCTATTGCAGAATGCTTCTTTACC (SEQ ID NO: 10) |
| Defa | Forward | GGTGATCATCAGACCCCAGCATCAGT (SEQ ID NO: 11) |
| | Reverse | AAGAGACTAAAACTGAGGAGCAGC (SEQ ID NO: 12) |
| Fasn | Forward | TTCCAAGACGAAAATGATGC (SEQ ID NO: 13) |
| | Reverse | AATTGTGGGATCAGGAGAGC (SEQ ID NO: 14) |
| Cpt1a | Forward | AGACCGTGAGGAACTCAAACCTAT (SEQ ID NO: 15) |
| | Reverse | TGAAGAGTCGCTCCCACT (SEQ ID NO: 16) |
| Pgc1a | Forward | AGCCGTGACCACTGACAACGAG (SEQ ID NO: 17) |
| | Reverse | GCTGCATGGTTCTGAGTGCTAAG (SEQ ID NO: 18) |
| Ppara | Forward | CAACGGCGTCGAAGACAAA (SEQ ID NO: 19) |
| | Reverse | TGACGGTCTCCACGGACAT (SEQ ID NO: 20) |
| Acox1 | Forward | CTATGGGATCAGCCAGAAAGG (SEQ ID NO: 21) |
| | Reverse | AGTCAAAGGCATCCACCAAAG (SEQ ID NO: 22) |
| Acc1 | Forward | TGTTGAGACGCTGGTTTGTAGAA (SEQ ID NO: 23) |
| | Reverse | GGTCCTTATTATTGTCCCAGACGTA (SEQ ID NO: 24) |
| Cebpa | Forward | GAGCCGAGATAAAGCCAAACA (SEQ ID NO: 25) |
| | Reverse | GCGCAGGCGGTCATTG (SEQ ID NO: 26) |
| G6pc | Forward | AGGAAGGATGGAGGAAGGAA (SEQ ID NO: 27) |
| | Reverse | TGGAACCAGATGGGAAAGAG (SEQ ID NO: 28) |

Insulin Resistance Index

Insulin resistance index was determined by multiplying the area under the curve (0 min and 15 min) of both blood glucose and plasma insulin obtained following an oral glucose load (2 g of glucose per kg of body weight) performed after 4 weeks (*A. muciniphila* study) of treatment. Food was removed two-hours after the onset of the daylight cycle and mice were treated after 6-h-fasting period as previously described (Everard et al. Diabetes 60, 2775-2786 (2011)).

Biochemical Analyses

Portal vein blood LPS concentration was measured by using Endosafe-MCS (Charles River Laboratories, Lyon, France) based on the Limulus amaebocyte Lysate (LAL) kinetic chromogenic methodology that measures color intensity directly related to the endotoxin concentration in a sample. Serum were diluted 1/10 with endotoxin free buffer to minimize interferences in the reaction (inhibition or enhancement) and heated 15 min at 70° C. Each sample was diluted 1/70 or 1/100 with endotoxin-free LAL reagent water (Charles River Laboratories) and treated in duplicate and two spikes for each sample were included in the determination. All samples have been validated for the recovery and the coefficient variation. The lower limit of detection was 0.005 EU/ml. Plasma insulin concentration was determined in 25 µl of plasma using an ELISA kit (Mercodia, Upssala, Sweden) according to the manufacturer instructions.

Fecal IgA levels were determined using an ELISA kit (E99-103, Bethyl Laboratories, Montgomery, TX). Freshly collected feces were frozen at −80° C. then diluted in 50 mM Tris, pH 7.4, 0.14M NaCl, 1% bovine serum albumin, 0.05% Tween 20. A 1/250 dilution was used to measure IgA by ELISA following the manufacturer instructions.

DNA Isolation From Mouse Cecal Samples

The cecal content of mice collected post mortem was stored at −80° C. Metagenomic DNA was extracted from the cecal content using a QIAamp-DNA stool mini-kit (Qiagen, Hilden, Germany) according to manufacturer's instructions.

Measurement of Endocannabinoids Intestinal Levels

Ileum tissues were homogenised in $CHCl_3$ (10 ml), and deuterated standards were added. The extraction and the calibration curves were generated as previously described (Muccioli et al, Mol Syst Biol, 2010, 6, 392), and the data were normalised by tissue sample weight.

qPCR: Primers and Conditions

The primers and probes used to detect *Akkermansia muciniphila* were based on 16S rRNA gene sequences: F-*Akkermansia muciniphila* CCTTGCGGTTGGCTTCA-GAT (SEQ ID NO: 29), R-*Akkermansia muciniphila*

CAGCACGTGAAGGTGGGGAC (SEQ ID NO: 30). Detection was achieved with StepOnePlus™ real-time PCR system and software (Applied Biosystems, Den Ijssel, The Netherlands) using Mesa Fast qPCR™ (Eurogentec, Seraing, Belgium) according to the manufacturer's instructions Each assay was performed in duplicate in the same run. The cycle threshold of each sample was then compared to a standard curve (performed in triplicate) made by diluting genomic DNA (five-fold serial dilution) (DSMZ, Braunshweig, Germany). The data are expressed as Log of bacteria/g of cecal content.

MITChip: PCR Primers and Conditions

DNA extracted from cecal contents was analyzed using the Mouse Intestinal Tract Chip (MITChip), a phylogenetic microarray consisting of 3,580 different oligonucleotides probes targeting two hypervariable regions of the 16S rRNA gene (V1 and V6 regions). Analysis of the MITChip were performed as previously described (Everard et al. Diabetes 60, 2775-2786 (2011); Geurts et al. Front Microbiol. 2, 149 (2011)). Briefly, Microbiota analysis was carried out on level 2 corresponding to genus-like level. Multivariate analysis was performed by representational difference analysis (RDA) as implemented in the CANOCO 4.5 software package (Biometris, Wageningen, The Netherlands) on average signal intensities for 99 bacterial groups (levels 2). All environmental variables were transformed as log (1+X). A Monte-Carlo permutation test based on 999 random permutations was used to test the significance. P values<0.05 were considered significant.

Measurement of Plasma Cholesterol

Plasma samples were assayed for cholesterol by measuring cholesterol present after enzymatic hydrolysis of ester cholesterol, using a commercial kit (DiaSys, Condom, France).

Statistical Analysis

Data are expressed as means±s.e.m. Differences between two groups were assessed using the unpaired two-tailed Student's t-test. Data sets involving more than two groups were assessed by ANOVA followed by Newman-Keuls post hoc tests. Correlations were analyzed using Pearson's correlation. Data with different superscript letters are significantly different P<0.05, according to the post-hoc ANOVA statistical analysis. Data were analyzed using GraphPad Prism version 5.00 for windows (GraphPad Software, San Diego, CA, USA). Results were considered statistically significant when P<0.05.

Results

Figure 1B:
Figure 1C:
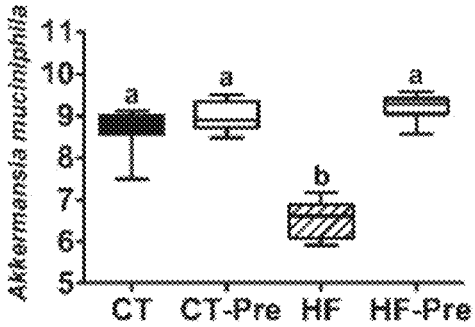
Figure 1D:
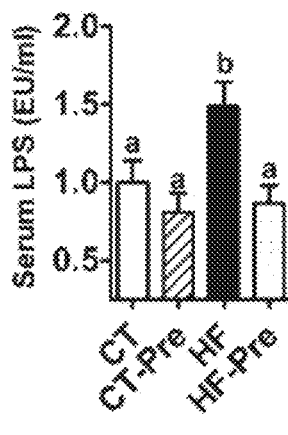
Figure 1E:
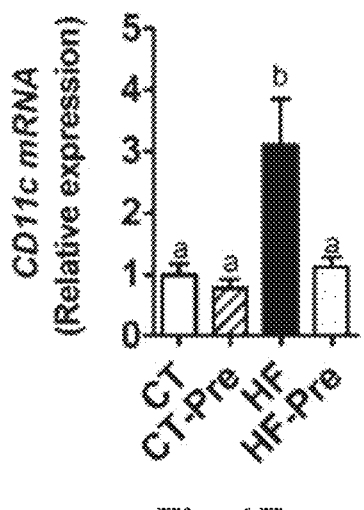
(FIG. 1E) Adipose tissue macrophages infiltration marker CD11c mRNA (n=10).
Figure 1F:
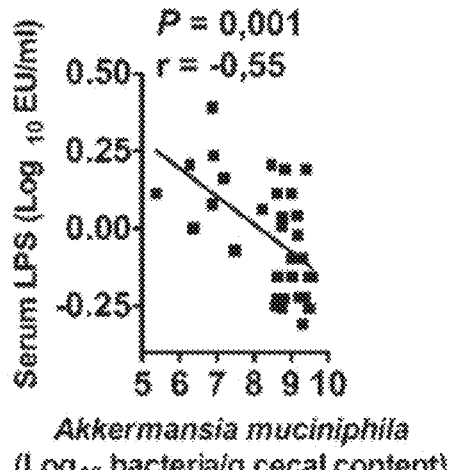
(FIG. 1F) Pearson's correlation between log values of portal vein LPS levels and *Akkermansia muciniphila* abundance ($Log_{10}$ of bacteria per g of cecal content), inset indicates Pearson's correlation coefficient (r) and the corresponding P value.
Figure 1G:
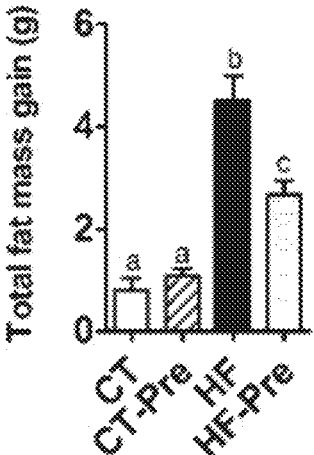
(FIG. 1G) Total fat mass gain measured by time-domain nuclear magnetic resonance (n=10). Data in FIGS. 1A-1C are shown as boxplots. *P<0.05, by two-tailed student t-test. Data in c-g have been obtained in the same group of mice. Data in FIGS. 1D, 1E, and 1G are shown as mean±s.e.m. Data with different superscript letters are significantly different (P<0.05), according to the post-hoc ANOVA one-way statistical analysis.

We found that abundance of A. muciniphila was 3300-fold lower in leptin-deficient obese mice versus their lean littermates (FIG. 1a). Consistently, we found a 100-fold decrease in high-fat (HF)-fed mice (FIG. 1c). In both models, prebiotics completely restore A. muciniphila count (FIG. 1b,c). In HF-fed mice, prebiotics abolished metabolic endotoxemia (FIG. 1d), normalized adipose tissue CD11c subpopulation of macrophages (FIG. 1e) and lowered fat mass (FIG. 1g and FIG. 3b). These results were significantly and inversely correlated with A. muciniphila (FIG. 1f and FIG. 3a,c). Nevertheless, it remained to demonstrate whether molecular mechanisms underlying the onset of these disorders rely on the lack of A. muciniphila and in contrast if the improvement after prebiotic treatment results from its higher abundance.

To address this question, A. muciniphila was orally administered to control or HF-fed mice during four weeks, thereby increasing A. muciniphila (FIGS. 4a,b). By using a phylogenetic-microarray (MITChip) (Everard et al. Diabetes 60, 2775-2786 (2011); Geurts et al. Front Microbiol. 2, 149 (2011)), we found that both HF-diet and A. muciniphila colonization significantly affected the complex relationship among bacteria within the gut microbiota composition, as shown by principal component analyses (PCA) (FIG. 2a) and supported by relative changes of different taxa.

Figures 2A, 2B, 2C, 2D, 2E, 2F:
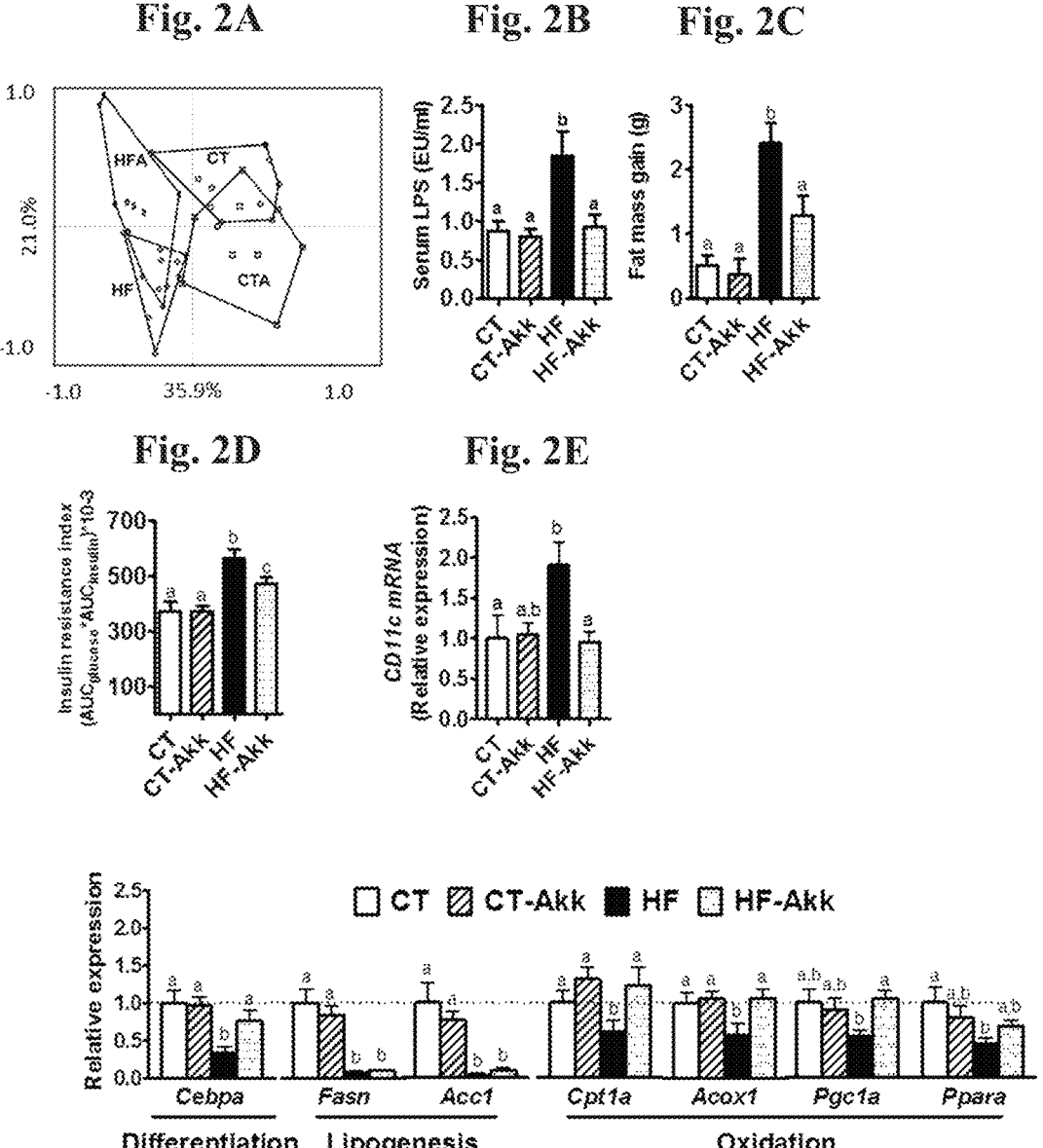
FIGS. 2A-2F are a combination of graphs and pictures showing that *Akkermansia muciniphila* changes gut microbiota composition, counteracts diet-induced gut barrier dysfunction, changes intestinal level of endocannabinoids and improves metabolic disorders in diet-induced obese mice. Mice were treated by daily oral gavage with *Akkermansia muciniphila* ($2\cdot10^8$ bacterial cells suspended in 200 µl sterile anaerobic phosphate buffer saline (PBS)) and fed a control diet (CT-Akk) or a HF-diet (HF-Akk) compared to mice fed a control diet (CT) or a high-fat diet (HF) and treated by daily oral gavage with an equivalent volume of sterile anaerobic PBS for 4-weeks (n=10).
Figures 5A, 5B, 5C, 5D:
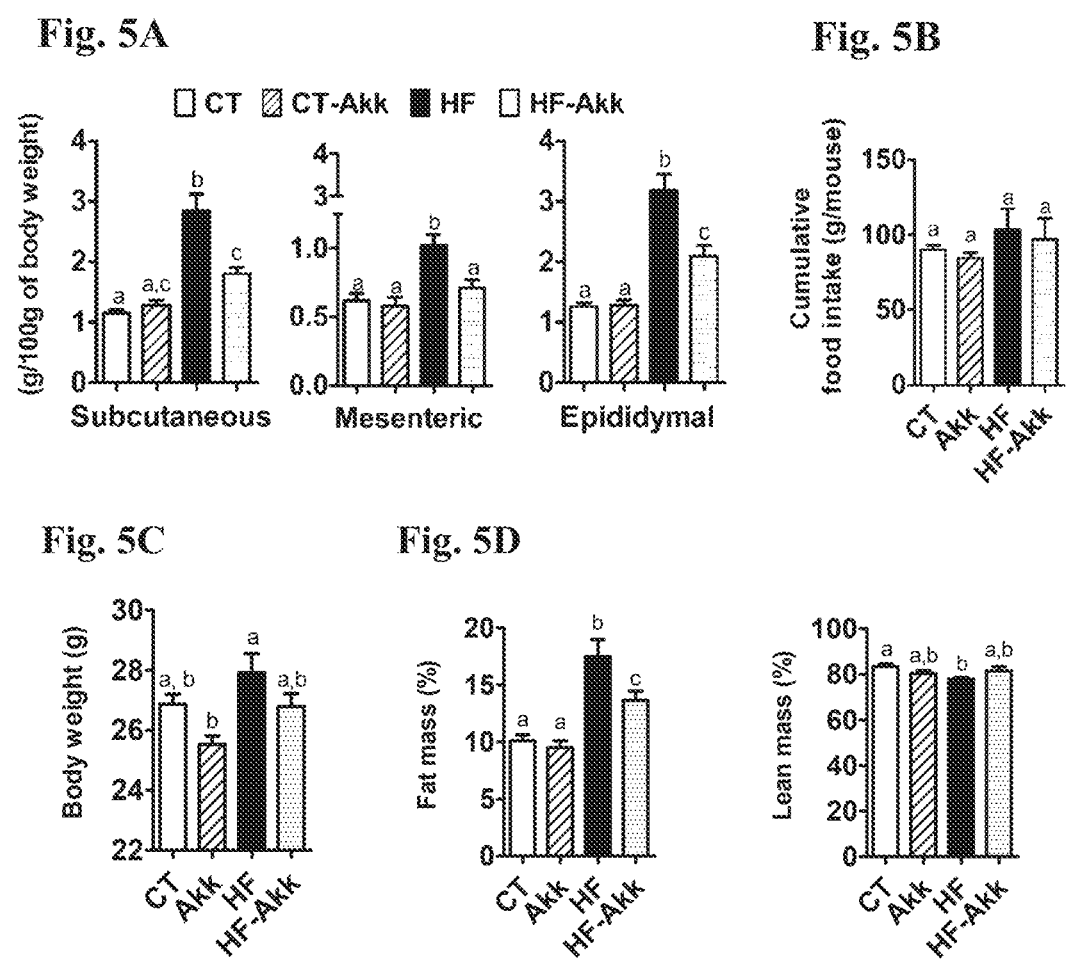

We found that A. muciniphila treatment normalized diet-induced metabolic endotoxemia, adiposity and adipose tissue CD11c marker (FIG. 2b,c,e and FIG. 5a), without any changes in food intake (FIG. 5b). Moreover, A. muciniphila treatment reduced body weight and improved body composition (i.e. fat mass/lean mass ratio) (FIGS. 5c and 5d). Accordingly, we hypothesized that A. muciniphila would impact on adipose tissue metabolism, and found that under HF-diet, A. muciniphila increased mRNA expression of markers of adipocyte differentiation and lipid oxidation without affecting lipogenesis (FIG. 2f). Together, these data further suggest that A. muciniphila controls fat storage and adipose tissue metabolism.

We next discovered that colonization with A. muciniphila completely reversed diet-induced fasting hyperglycemia, by a mechanism associated with a 40% reduction of hepatic glucose-6-phosphatase expression (FIG. 6a,b), thereby suggesting reduced gluconeogenesis. Notably, the insulin-resistance index was similarly reduced after treatment (FIG. 2d). Collectively, these results suggest that A. muciniphila contributes to regulation of adipose tissue metabolism and glucose homeostasis. One explanation would be that A. muciniphila plays key roles at different levels of the regulation of gut barrier function. Recent data suggest that intestinal cells also contribute to the maintenance of gut barrier by secreting antimicrobial peptides thereby shaping microbial communities (Pott et al, EMBO Rep (2012)).

Figures 7A, 7B, 7C:
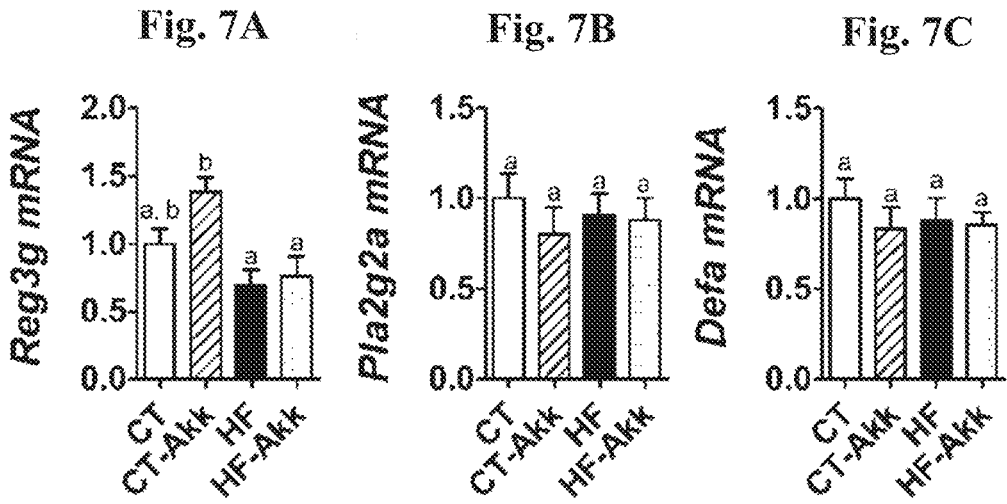
Figures 7D, 7E:
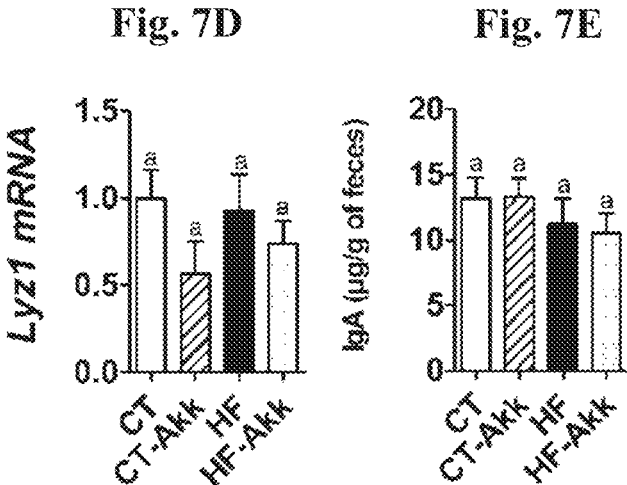

To further elucidate how A. muciniphila colonization affects gut barrier function; we measured the expression of Paneth and epithelial cells antibacterial markers in the ileum. We found that A. muciniphila increased Reg3g (regenerating islet-derived 3-gamma, RegIIIγ) expression under control diet, whereas this effect was not observed in HF-fed mice (FIG. 7a). Pla2g2a, Defa expression were similar between groups, whereas Lyz1 expression tends to be lower after bacteria administration (FIG. 7b,c,d). IgA are secreted in intestinal lumen and are known to restrict mucosal bacterial penetration (Vaishnava, S., et al. Science 334, 255-258 (2011)), here we found that fecal IgA levels were not affected by the treatments (FIG. 7e). Thereby, suggesting that A. muciniphila controls gut barrier function by other mechanisms involving its epithelial signalling (Derrien et al. Front Microbiol 2, 166 (2011)). We may not rule out that the endocannabinoid system plays a crucial role in this context; since we found that A. muciniphila treatment increased 2-oleoylglycerol, 2-palmitoylglycerol and 2-arachidonoylglycerol intestinal levels (FIG. 2g). Importantly, 2-oleoylglycerol has been shown to stimulate glucagon-like peptide-1 (GLP-1) release from intestinal L-cells suggesting that both GLP-1 and GLP-2 might improve gut barrier and glucose homeostasis in this context (Hansen, et al. J Clin Endocrinol Metab 96, E1409-1417 (2011)). Moreover, 2-arachidonoylglycerol reduces gut permeability and 2-palmitoylglycerol (Alhouayek et al FASEB J 25, 2711-2721 (2011); Ben-Shabat, et al. Eur. J. Pharmacol. 353, 23-31 (1998)) potentiates 2-arachidonoylglycerol anti-inflammatory effects. Therefore, it is likely that the increased levels of these three endocannabinoids observed after A. muciniphila colonization constitutes a molecular event linking these metabolic features.

Recent evidences support that interactions between gut microbiota and mucus layer are dynamic systems affecting the biology of mucus barrier (Belzer et al, ISME J 6, 1449-1458 (2012); Johansson et al, Proc Natl Acad Sci USA 108 Suppl 1, 4659-4665 (2011)). Thus we investigated the impact of *A. muciniphila* colonization on the inner mucus layer thickness. Remarkably, we found a 46% thinner mucus layer in HF-fed mice (FIG. 2*h*), whereas *A. muciniphila* colonization counteracts this decrease (FIG. 2*h*). Together these novel findings support the idea that the presence of *A. muciniphila* within mucus layer is a crucial mechanism to control mucus turnover (Belzer et al, ISME J 6, 1449-1458 (2012)). We next examined whether *A. muciniphila* also affects Reg3g expression in the colon epithelial cells. Strikingly, Reg3g expression was reduced by about 50% under HF-diet. *A. muciniphila* completely blunted this effect and even more increased Reg3g expression by 400% as compared to HF-fed mice (FIG. 2*i*). Thus this links the colonization of the colon, but not ileum, by *A. muciniphila* with the fundamental immune mechanism by which RegIIIγ promotes host-bacterial mutualism and regulates the spatial relationships between microbiota and host (Vaishnava, S., et al. Science 334, 255-258 (2011)). It is important to note that in germ-free mice *A. muciniphila* induces gene expression in the colon rather than the ileum (Derrien et al. Front Microbiol 2, 166 (2011)).

Figure 8A:
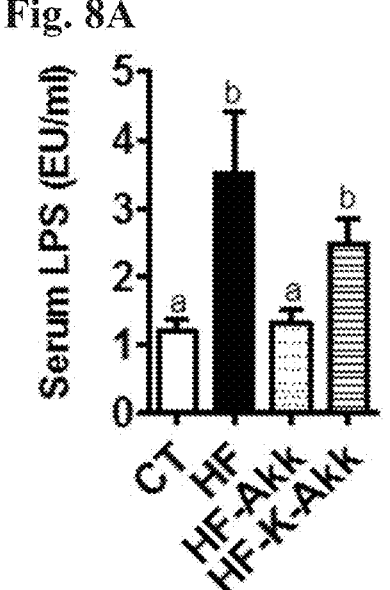
Figure 8B:
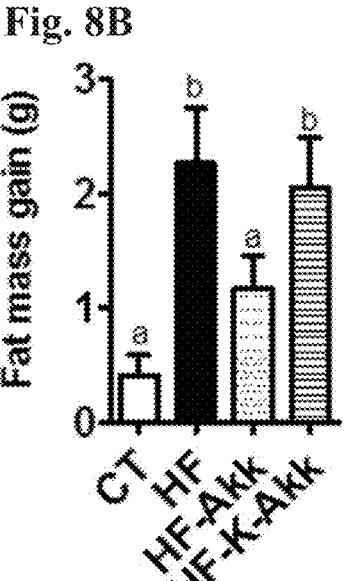
Figure 8C:
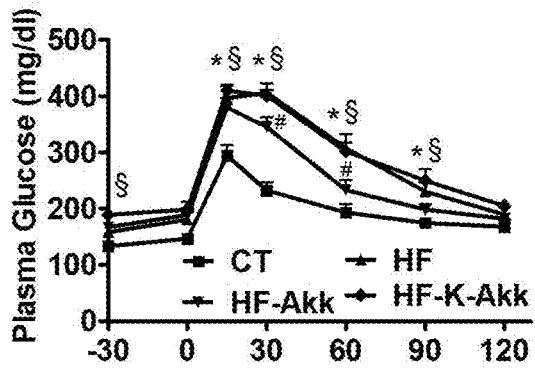
Figure 8D:
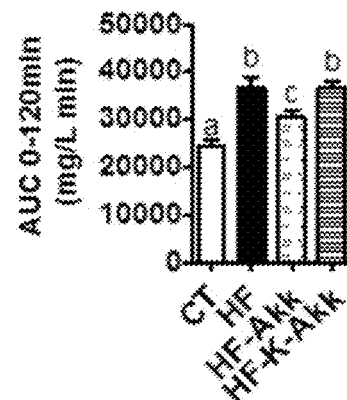
Figure 8E:
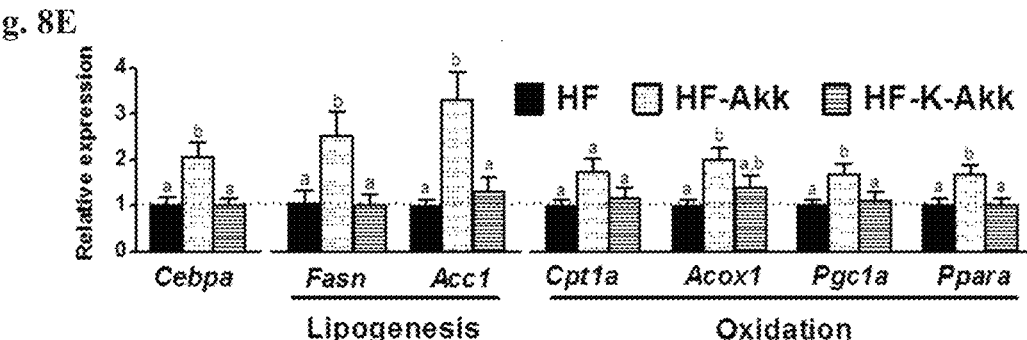
Figure 8F:
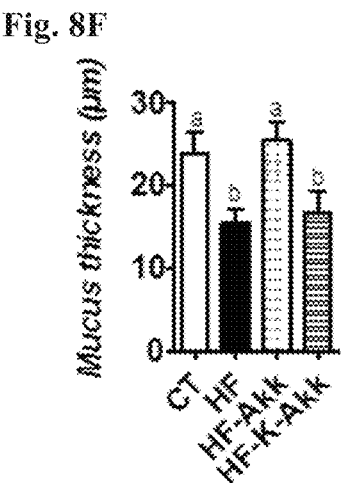
Figure 8G:
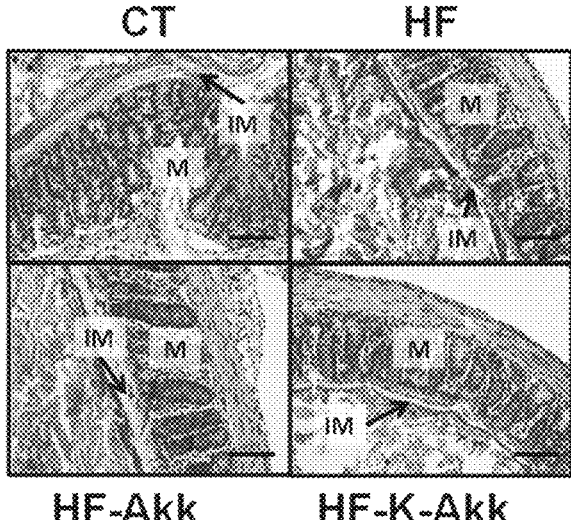

To further demonstrate whether *A. muciniphila* has to be alive to exert its metabolic effects, we have compared the impact of viable *A. muciniphila* administration ($2 \cdot 10^8$ bacterial cells suspended in 200 μl of sterile anaerobic phosphate-buffered saline (PBS)) to heat-killed/inactivated *A. muciniphila* (autoclaving, 15 minutes, 121° C., 225 kPa). We found that viable and metabolically active *A. muciniphila* counteracted diet-induced metabolic endotoxemia, fat mass development and altered adipose tissue metabolism (FIG. 8A, B, D and FIG. 9A) to a similar extent as observed in the first set of experiments. Importantly, these effects were not observed following the administration of heat-inactivated *A. muciniphila* (FIGS. 8A, B, D and FIG. 9A). In addition, we found that metabolically active *A. muciniphila* significantly reduced plasma glucose levels following an oral glucose tolerance test (FIG. 8C), whereas heat-inactivated *A. muciniphila* exhibited similar glucose intolerance than HF-fed mice (FIG. 8C). Finally, we confirmed that metabolically active *A. muciniphila* restored mucus layer thickness upon HF-diet whereas we found that heat-inactivated *A. muciniphila* did not improve mucus layer thickness as compared to HF (FIGS. 8E and F). It is worth noting that we found 100-fold more metabolically active *A. muciniphila* recovered from the cecal and colonic content of *A. muciniphila* treated mice as compared to HF and heat-inactivated bacteria group (HF-Akk: 9.5+/−1.02 $\text{Log}_{10}$ cells/mg of content, HF and HF-K-Akk: 6.8+/−0.51 $\text{Log}_{10}$ cells/mg of content, P=0.0059), thereby evidencing the viability of *A. muciniphila* after oral administration.

These results thus confirm that that HF diet-induced obesity is associated with changes in gut microbiota composition, however, antimicrobial peptides in the ileum were not affected by the treatments. In contrast, Reg3g expression in colon epithelial cells was significantly reduced by approximately 50% in HF and heat-inactivated *A. muciniphila* treated mice, whereas metabolically active *A. muciniphila* treatment completely blunted this effect and increased Reg3g expression upon HF diet (FIG. 9B).

We then wanted to test if *A. muciniphila* administration was still efficient during a prolonged high-fat diet treatment (8 weeks) and if the administration of *A. muciniphila* 3 times a week (instead of daily) was sufficient to protect against diet-induced obesity. The preparations as well as the doses of *A. muciniphila* were similar to those presented in the protocol using daily oral gavage or metabolically inactivated *A. muciniphila*.

We found that *A. muciniphila* treatment reduces body weight gain (FIG. 10A) by about 30% although mice were ingesting high-fat diet without any fat lost in their feces and changes in food intake behavior. This was also associated with a reduction of about 45% of the adipose tissue weight (subcutaneous adipose tissue) (FIG. 10B) and 35% decrease in visceral fat depots (mesenteric and epididymal) (FIG. 10C). Thus, this set of data support the fact that *A. muciniphila* administration remains efficient during a prolonged treatment and the treatment is still efficient if *A. muciniphila* is administered 3 times per week instead of daily.

In order to confirm that these results were specific of *A. muciniphila*, we then treated HF-fed mice with a probiotic (i.e. *Lactobacillus plantarum* WCFS1). We found that *L. plantarum* administration did not change fat mass development, adipose tissue metabolism, mucus layer thickness, colon Reg3g mRNA, and metabolic endotoxemia (FIG. 12A-E).

Hypercholesterolemia is known as a key factor involved in cardiovascular diseases. We therefore tested the effect of *A. muciniphila* administration on plasma cholesterol of mice fed a high-fat diet. As shown in FIG. 11, *A. muciniphila* treatment significantly decreases (about 15%) plasma cholesterol, thereby contributing with LPS and the other metabolic parameters to an improved cardio-metabolic risk profile.

In summary, our findings not only provide substantial insights into the intricate mechanisms by which *A. muciniphila* regulates the crosstalk between the host and the gut microbiota, but also provide a rationale for considering the development of a treatment using this human mucus-colonizer for the prevention or the treatment of obesity and associated metabolic disorders such as, for example, hypercholesterolemia.

---

The invention claimed is:

1. A method for promoting weight loss in a subject in need thereof, the method comprising orally administering a composition comprising an effective amount of bacteria comprising substantially purified *Akkermansia* to the subject, wherein the substantially purified *Akkermansia* comprises at least 50% of a strain of *Akkermansia*, thereby promoting weight loss in the subject.

2. The method of claim 1, wherein the amount of bacteria comprises at least 50% *Akkermansia muciniphila* or fragments thereof.

3. The method of claim 1, wherein said method does not impact the food intake of said subject.

4. The method of claim 1, wherein viable cells of *Akkermansia muciniphila* are administered to the subject.

5. The method of claim 1, wherein *Akkermansia muciniphila* are orally administered to the subject.

6. The method of claim 1, wherein an amount of *Akkermansia muciniphila* ranging from about $1 \cdot 10^4$ to about $1 \cdot 10^{12}$ cfu is administered to the subject.

7. The method of claim 1, wherein *Akkermansia muciniphila* are administered at least three times a week.

8. The method of claim 1, wherein the subject is a human.

9. The method of claim 1, wherein *Akkermansia muciniphila* are co-administered with a probiotic strain in addition to the *Akkermansia muciniphila*.

10. The method of claim 1, wherein *Akkermansia muciniphila* are co-administered with one or more prebiotics.

* * * * *